US012364725B2

(12) United States Patent
Engholdt

(10) Patent No.: US 12,364,725 B2
(45) Date of Patent: Jul. 22, 2025

(54) METHODS OF INHIBITING CANCER GROWTH AND INHIBITING VIRAL INFECTIONS

(71) Applicant: Infinitum Health, LLC, Phoenix, AZ (US)

(72) Inventor: Kevin Thomas Engholdt, Phoenix, AZ (US)

(73) Assignee: Infinitum Health, LLC, Phoenix, AZ (US)

( * ) Notice: Subject to any disclaimer, the term of this patent is extended or adjusted under 35 U.S.C. 154(b) by 0 days.

(21) Appl. No.: 18/806,538

(22) Filed: Aug. 15, 2024

(65) Prior Publication Data

US 2024/0398881 A1    Dec. 5, 2024

Related U.S. Application Data

(63) Continuation of application No. PCT/US2024/015624, filed on Feb. 13, 2024.

(60) Provisional application No. 63/485,452, filed on Feb. 16, 2023.

(51) Int. Cl.
| | |
|---|---|
| A61K 36/74 | (2006.01) |
| A61K 36/03 | (2006.01) |
| A61K 36/04 | (2006.01) |
| A61K 36/068 | (2006.01) |
| A61K 36/074 | (2006.01) |
| A61K 36/889 | (2006.01) |
| A61P 31/14 | (2006.01) |
| A61P 31/16 | (2006.01) |
| A61P 31/20 | (2006.01) |
| A61P 31/22 | (2006.01) |
| A61P 35/00 | (2006.01) |

(52) U.S. Cl.
CPC ............ *A61K 36/074* (2013.01); *A61K 36/03* (2013.01); *A61K 36/04* (2013.01); *A61K 36/068* (2013.01); *A61K 36/889* (2013.01); *A61P 31/14* (2018.01); *A61P 31/16* (2018.01); *A61P 31/20* (2018.01); *A61P 31/22* (2018.01); *A61P 35/00* (2018.01)

(58) Field of Classification Search
None
See application file for complete search history.

(56) References Cited

U.S. PATENT DOCUMENTS

| | | | |
|---|---|---|---|
| 5,445,829 A | 8/1995 | Paradissis et al. | |
| 5,576,012 A | 11/1996 | Bauer et al. | |
| 5,601,845 A | 2/1997 | Buxton et al. | |
| 5,641,515 A | 6/1997 | Ramtoola | |
| 5,653,987 A | 8/1997 | Modi et al. | |
| 5,654,286 A | 8/1997 | Hostetler | |
| 5,667,809 A | 9/1997 | Trevino et al. | |
| 5,707,615 A | 1/1998 | Cardin et al. | |
| 5,707,641 A | 1/1998 | Gertner et al. | |
| 5,726,181 A | 3/1998 | Hausheer et al. | |
| 5,733,888 A | 3/1998 | Carver et al. | |
| 2003/0104005 A1* | 6/2003 | Goino | A61P 43/00 424/728 |
| 2016/0038530 A1 | 2/2016 | Engholdt | |
| 2018/0168198 A1 | 6/2018 | Petralia | |
| 2019/0343906 A1 | 11/2019 | Li et al. | |
| 2022/0290249 A1 | 9/2022 | Shimura et al. | |

FOREIGN PATENT DOCUMENTS

| | | |
|---|---|---|
| WO | WO 2022/002867 A1 | 1/2022 |
| WO | WO 2022/272114 A1 | 12/2022 |

OTHER PUBLICATIONS

Athukorala (Molecules (2016), vol. 21, No. 119, 17 pages).*
Mathew (Integrative Cancer Therapies (2017), vol. 16, No. 4, pp. 572-584).*
Richards, et al., "Oral Fucoidan Attenuates Lung Pathology and Clinical Signs in a Severe Influenza a Mouse Model," Marine Drugs, May 8, 2020, vol. 18, 246, pp. 1-10.
International Search Report mailed on Jul. 10, 2024 in PCT/US2024/015624, filed Feb. 13, 2024.
U.S. Appl. No. 16/792,745, filed Feb. 17, 2020, Engholdt.
Ahmad, 2020, Ganoderma lucidum: A rational pharmacological approach to surmount cancer. J Ethnopharmacol. 260:113047, 450 pp.
Al Monla et al., 2022, Fucoidan and Alginate from the Brown Algae Colpomenia sinuosa and Their Combination with Vitamin C Trigger Apoptosis in Colon Cancer. Molecules. 27:358.
Alessandra-Perini et al., 2018, Anticancer potential, molecular mechanisms and toxicity of Euterpe oleracea extract (acai): A systematic review. PLoS ONE 13(7):e0200101.
Alm et al., 1989, Effects of topically applied $PGF_{2\alpha}$ and its isopropylester on normal and glaucomatous human eyes, Prog. Clin. Biol. Res., 312:447-458.
Alonso et al., 2018, Antitumoral and antimetastatic activity of Maitake D-Fraction in triple-negative breast cancer cells. Oncotarget, 9(34):23396-23412.
Atashrazm et al., Apr. 2015, Fucoidan and cancer: a multifunctional molecule with anti-tumor potential. Mar Drugs. 13(4):2327-2346.
Bae et al., Jan. 2020, Fucoidan Derived from Fucus vesiculosus Inhibits the Development of Human Ovarian Cancer via the Disturbance of Calcium Homeostasis, Endoplasmic Reticulum Stress, and Angiogenesis. Mar Drugs. 18(1):45.

(Continued)

*Primary Examiner* — Susan Hoffman
(74) *Attorney, Agent, or Firm* — Knobbe, Martens, Olson & Bear, LLP

(57) ABSTRACT

Provided herein are methods and compositions related to inhibiting cancer growth and to treating cancer in a subject. Further provided herein are methods and compositions related to reducing viral load and to inhibiting attachment of enveloped viruses in an individual. In some embodiments, compositions describe herein include an effective amount of one or more of *Laminaria japonica*, *Undaria pinnatifida*, *Palmaria palmata*, *Fucus vesiculosus*, *Grifola frondosa*, *Ganoderma lucidum*, *Hericium erinaceus*, *Cordyceps sinensis*, and *Euterpe oleracea*.

20 Claims, 2 Drawing Sheets

(56) References Cited

OTHER PUBLICATIONS

Barbieri et al., 2017, Anticancer and Anti-Inflammatory Properties of Ganoderma lucidum Extract Effects on Melanoma and Triple-Negative Breast Cancer Treatment. Nutrients. 9(3):210.
Bie et al., 2020, A polysaccharide from Grifola frondosa fruit body induces HT-29 cells apoptosis by PI3K/AKT-MAPKs and NF-κB-pathway. Int J Biol Macromol. 147:79-88.
Blaszczak et al., 2018, Fucoidan Exerts Anticancer Effects Against Head and Neck Squamous Cell Carcinoma In Vitro. Molecules. 23(12):3302.
Boo et al., Aug. 2013, The anticancer effect of fucoidan in PC-3 prostate cancer cells. Mar Drugs. 11(8):2982-2999.
Chantree et al., Aug. 2020, Antitumor Effects of Fucoidan Via Apoptotic and Autophagic Induction on HSC-3 Oral Squamous Cell Carcinoma. Asian Pac J Cancer Prev. 21(8):2469-2477.
Chantree et al., Jan. 2021, Anticancer Activity of Fucoidan via Apoptosis and Cell Cycle Arrest on Cholangiocarcinoma Cell. Asian Pac J Cancer Prev. 22(1):209-217.
Chen et al., 2014, The Effect of Mushroom Beta-Glucans from Solid Culture of Ganoderma lucidum on Inhibition of the Primary Tumor Metastasis. Evid Based Complement Alternat Med. 2014:252171.
Chia et al., 2021, A small molecule, ACAi-028, with anti-HIV-1 activity targets a novel hydrophobic pocket on HIV-1 capsid. Antimicrob Agents Chemother, 65:e01039-21.
Chollet et al., 2016, Fucoidans in Nanomedicine. Mar. Drugs. 14:145.
Cumashi et al., 2007, A comparative study of the anti-inflammatory, anticoagulant, antiangiogenic, and antiadhesive activities of nine different fucoidans from brown seaweeds. Glycobiology. 17(5):541-552.
Da Silva et al., 2022, Ultrastructural changes induced by açai (*Euterpe oleracea Mart*) in MCF-7 breast cancer cell line, Ultrastructural Pathology. 46(6):511-518.
Da Silva et al., 2021, Açai (*Euterpe oleracea Mart.*) Seed Extract Induces ROS Production and Cell Death in MCF-7 Breast Cancer Cell Line. Molecules, 26:3546.
De Camargo et al., 2022, Ganoderma lucidum polysaccharides inhibit in vitro tumorigenesis, cancer stem cell properties and epithelial-mesenchymal transition in oral squamous cell carcinoma. J Ethnopharmacol. 286:114891.
Deng et al., 2009, A phase I/II trial of a polysaccharide extract from *Grifola frondosa* (Maitake mushroom) in breast cancer patients: immunological effects. J Cancer Res Clin Oncol. 135(9):1215-1221.
Didukh et al., 2003, Medicinal value of species of the family Agaricaceae Cohn (higher Basidiomycetes) current stage of knowledge and future perspectives. Int J Med Mushrooms. 5:133-152.
Dos Santos et al., 2022, Nutraceutical potential of Amazonian oilseeds in modulating the immune system against COVID-19—A narrative review. J Funct Foods. 94:105123.
Dotan et al., 2011, The culinary-medicinal mushroom *Coprinus comatus* as a natural antiandrogenic modulator. Integr Cancer Ther. 10(2)::148-159.
Duan et al., 2017, Induction Effect to Apoptosis by Maitake Polysaccharide: Synergistic Effect of Its Combination With Vitamin C in Neuroglioma Cell. J Evid Based Complementary Altern Med. 22(4):667-674.
El-Mekkawy et al., 1998, Anti-HIV-1 and anti-HIV-1-protease substances from Ganoderma lucidum. Phytochemistry 49(6):1651-1657.
Engholdt et al., Oct. 27-29, 2018, Nutritional supplement to complement cancer therapy, Poster, 2 pp.
Ferreira et al., 2015, Structure-function relationships of immunostimulatory polysaccharides: A review. Carbohydr Polym. 5:132:378-396 with errata.
Fingl et al., 1975, Chapter 1. General Principles, in The Pharmacological Basis of Therapeutics, Goodman et al., eds., MacMillan Publishing Co., Inc., New York, 49 pp.
Fitton et al., 2015, Therapies from fucoidan: An update. Mar. Drugs. 13:5920-5946.
Fitton, 2011, Therapies from fucoidan; multifunctional marine polymers. Mar Drugs. 9(10):1731-1760.
Fleurence et al., 2016, Seaweed in Health and Disease Prevention. Academic Press.
Gao et al., 2002, A Phase I/II study of a Ganoderma lucidum extract (Ganopoly) in patients with advanced cancer. IntJ Med Mushrooms, 4:207-214.
Gao et al., 2003, Antibacterial and antiviral value of the genus *Ganoderma P. Karst*. species (Aphyllophoromycetideae): a review. Int J Med Mushrooms. 5:235-246.
Gao et al., 2004, A phase I/II study of Ling Zhi mushroom *Ganoderma lucidum* (W.Curt.:Fr.) Lloyd (Aphyllophoromycetideae) extract in patients with type II diabetes mellitus. Int J Med Mushrooms 6:33-39.
Gill et al., Jun. 2017, Ganoderma lucidum targeting lung cancer signaling: A review. Tumour Biol. 39(6):1-10.
Gill et al., Mar. 2017, Ganoderic acid targeting nuclear factor erythroid 2-related factor 2 in lung cancer. Tumour Biol. 39(3):1010428317695530.
Guven et al., 2020. Pharmacology of marine macroalgae. Encyclopedia of Marine Biotechnology, 1:585-615.
Hans et al., 2021, Antiviral activity of sulfated polysaccharides from marine algae and its application in combating COVID-19: Mini review, Bioresource Technology Reports, 13:100623.
Harden et al., Sep. 2009, Virucidal activity of polysaccharide extracts from four algal species against herpes simplex virus. Antiviral Res. 83(3):282-289.
He et al., 2017, Structures, biological activities, and industrial applications of the polysaccharides from *Hericium erinaceus* (Lion's Mane) mushroom: A review, International Journal of Biological Macromolecules, 97:228-237.
He et al., 2019, Chapter 11. The biological activities of the antitumor drug Grifola frondosa polysaccharide. in Progress in Molecular Biology and Translational Science, vol. 163 Elsevier Inc., pp. 221-261.
Hemmingson et al., 2006, Structure and antiviral activity of the galactofucan sulfates extracted from Undaria pinnatifida (Phaeophyta). J. Appl. Phycol. 18:185-193.
Hetland et al., Jan. 2021, Can medicinal mushrooms have prophylactic or therapeutic effect against COVID-19 and its pneumonic superinfection and complicating inflammation? Scand J Immunol. 93(1):e12937.
Ho et al., 2022, Ganoderma microsporum immunomodulatory protein acts as a multifunctional broad-spectrum antiviral against SARS-CoV-2 by interfering virus binding to the host cells and spike-mediated cell fusion, Biomedicine & Pharmacotherapy, 155:113766.
Hsu et al., 2018, Fucoidan upregulates TLR4/CHOP-mediated caspase-3 and PARP activation to enhance cisplatin-induced cytotoxicity in human lung cancer cells. Cancer Lett. 432:112-120.
Hsu et al., 2019, Clinical applications of fucoidan in translational medicine for adjuvant cancer therapy. Clin Trans Med, 8: e15.
Hsu et al., 2020, Fucoidan from Laminaria japonica exerts antitumor effects on angiogenesis and micrometastasis in triple-negative breast cancer cells. Int J Biol Macromol. 149:600-608.
Hu et al., 2022, Effect of Maitake D-fraction in advanced laryngeal and pharyngeal cancers during concurrent chemoradiotherapy: A randomized clinical trial. Acta Biochim Pol. 69(3):625-632.
Infinimin Health LLC, Jun. 2013, product label, 1 p.
Infinitum Health Team, Jun. 7, 2014, Resihi muschroom protects against hair loss in complement to traditional radiation therapy, https://web.archive.org/web/20230203095847/https://www.infinitumhealth.com/post/2016/03/01/reishi-mushroom-protects-against-hair-loss-in-comple . . . , 4 pp.
Irhimeh et al., 2009, Pilot clinical study to evaluate the anticoagulant activity of fucoidan. Blood Coagul. Fibrinolysis, 20:607-610.
Jang et al., Nov. 15, 2019, Cordycepin inhibits human ovarian cancer by inducing autophagy and apoptosis through Dickkopf-related protein 1/β-catenin signaling. Am J Transl Res. 11(11):6890-6906.
Jeitler et al., Nov. 11, 2020, Significance of Medicinal Mushrooms in Integrative Oncology: A Narrative Review, 11:580656.

(56) References Cited

OTHER PUBLICATIONS

Jiang et al., 2010, Novel medicinal mushroom blend suppresses growth and invasiveness of human breast cancer cells. Int J Oncol. 37(6):1529-1536.
Jin et al., 2022, Seaweeds in the Oncology Arena: Anti-Cancer Potential of Fucoidan as a Drug—A Review. Molecules. 27(18):6032.
Jobim et al., 2019, Acai (*Euterpe oleracea, Mart.*), an Amazonian fruit has antitumor effects on prostate cancer cells. Arch. Biosci. Health. 1:61-76.
Joshi et al., 1994, Microparticulates for Opththalmic drug delivery, J. Ocul. Pharmacol., 10(1):29-45.
Kiselevskiy et al., 2022, Prospects for the Use of Marine Sulfated Fucose-Rich Polysaccharides in Treatment and Prevention of COVID-19 and Post-COVID-19 Syndrome. Russ J Bioorg Chem. 48(6):1109-1122.
Kladar et al., 2016, Ganoderma: insights into anticancer effects. Eur J Cancer Prev. 25(5):462-471.
Konno, 2009, Synergistic potentiation of D-fraction with vitamin C as possible alternative approach for cancer therapy. Int J Gen Med. 30:91-108.
Krupodorova et al., 2014, Antiviral activity of Basidiomycete mycelia against infuenza type A (serotype H1N1) and herpes simplex virus type 2 in cell culture. Virol. Sin. 29(5):284-290.
Kwon et al., 2020, Sulfated polysaccharides effectively inhibit SARS-CoV-2 in vitro. Cell Discov 6:50.
Li et al., 2008, Fucoidan: structure and bioactivity. Molecules. 13(8):1671-1695.
Li et al., 2017, Fucoidan from Fucus vesiculosus suppresses hepatitis B virus replication by enhancing extracellular signal-regulated Kinase activation. Virol J. 14(1):178.
Li et al., 2020, Cordycepin inhibits pancreatic cancer cell growth in vitro and in vivo via targeting FGFR2 and blocking ERK signaling. Chin J Nat Med. 18(5):345-355.
Liang et al., 2016, Low molecular weight fucoidan ameliorates streptozotocin-induced hyper-responsiveness of aortic smooth muscles in type 1 diabetes rats. J. Ethnopharmacol. 191:341-349.
Lin et al., 2020, The anti-cancer effects of fucoidan: a review of both in vivo and in vitro investigations. Cancer Cell Int 20: 154.
Liu et al., 2022, Chinese Cordyceps: Bioactive Components, Antitumor Effects and Underlying Mechanism—A Review. Molecules. 27(19):6576.
Lopes et al., 2019, A New Look for the Red Macroalga Palmaria palmata: A Seafood with Polar Lipids Rich in EPA and with Antioxidant Properties. Mar Drugs. 17(9):533.
Ma et al., Apr. 2021, Fucoidan Inhibits the Progression of Hepatocellular Carcinoma via Causing IncRNA LINC00261 Overexpression, Frontiers in Oncology, 11:653902.
Makarenkova et al., 2010, Antiviral activity of sulfated polysaccharide from the brown algae *Laminaria japonica* against avian influenza A (H5N1) virus infection in the cultured cells. Voprosy virusologii. 55(1):41-45.
Mao et al., 2015, Antitumor and immunomodulatory activity of a water-soluble polysaccharide from Grifola frondosa. Carbohydr Polym., 134:406-412.
Mayer et al., 1996, Efficacy of a novel hydrogel formulation in human volunteers, Ophthalmologica, 210(2):101-103.
McLennan, Feb. 19, 2021, I had a kidney tumor and multiple cysts and was told I couldn't get pregnant . . . Until now, https://web.archive.org/web/20210304210012/https://www.infinitumhealth.com/post/2015/02/01/i-had-a-kidney-tumor-and-multiple-cysts-and-was-told-i . . . , 2 pp.
Millan-Linares et al., 2019, Nutraceutical Extract from Dulse (*Palmaria palmata* L.) Inhibits Primary Human Neutrophil Activation. Mar Drugs. 17(11):610.
Monge-Fuentes et al., 2017, Photodynamic therapy mediated by acai oil (*Euterpe oleracea Martius*) in nanoemulsion: A potential treatment for melanoma. J. Photochem. Photobiol. B Biol. 166:301-310.
Moran-Santibanez et al., 2018, Virucidal and synergistic activity of polyphenol-rich extracts of seaweeds against measles virus. Viruses. 10:465.
Myers et al., 2016, Effects of fucoidan from Fucus vesiculosus in reducing symptoms of osteoarthritis: A randomized placebo-controlled trial. Biol. Targets Ther. 10:81-88.
Na et al., May 2017, Anticarcinogenic effects of water extract of sporoderm-broken spores of Ganoderma lucidum on colorectal cancer in vitro and in vivo. Int J Oncol, 50(5):1541-1554.
Newman et al., 2007, Natural Products as Sources of New Drugs over the Last 25 Years, J. Nat. Prod., 70:461-477.
Oliveira et al., 2019, Fucoidan from Fucus vesiculosus inhibits new blood vessel formation and breast tumor growth in vivo. Carbohydr Polym. 223:115034.
Oliyaei et al., 2022, Therapeutic activity of fucoidan and carrageenan as marine algal polysaccharides against viruses. 3 Biotech. 12(7):154.
Pagarete et al., 2021, Antiviral Potential of Algal Metabolites—A Comprehensive Review. Mar. Drugs. 19:94.
Panwong et al., 2021, Cordycepin Sensitizes Cholangiocarcinoma Cells to Be Killed by Natural Killer-92 (NK-92) Cells. Molecules 26:5973.
Patel et al., 2012, Recent developments in mushrooms as anticancer therapeutics: a review. 3 Biotech. 2:1-15.
Phull et al., 2018, Undaria pinnatifida a Rich Marine Reservoir of Nutritional and Pharmacological Potential: Insights into Growth Signaling and Apoptosis Mechanisms in Cancer, Nutrition and Cancer, 70(6):956-970.
Pradhan et al., 2022, A state-of-the-art review on fucoidan as an antiviral agent to combat viral infections. Carbohydr Polym. 291:119551.
Prokofjeva et al., 2013, Fucoidans as potential inhibitors of HIV-1. Mar Drugs. 11(8):3000-3014.
Qi et al., 2020, Cordyceps sinensis polysaccharide inhibits colon cancer cells growth by inducing apoptosis and autophagy flux blockage via mTOR signaling, Carbohydrate Polymers, 237:116113.
Quan et al., 2020, Cordyceps militaris Induces Immunogenic Cell Death and Enhances Antitumor Immunogenic Response in Breast Cancer, Evidence-Based Complementary and Alternative Medicine, 2020:9053274, 11 pages.
Queiroz et al., 2008, Inhibition of reverse transcriptase activity of HIV by polysaccharides of brown algae, Biomedicine & Pharmacotherapy, 62(5):303-307.
Rahman et al., 2021, Rationalization of Mushroom-Based Preventive and Therapeutic Approaches to COVID-19: Review. Int J Med Mushrooms. 23(5):1-11.
Remigante et al., 2022, Acai (*Euterpe oleracea*) Extract Protects Human Erythrocytes from Age-Related Oxidative Stress. Cells. 11:2391.
Remington's Pharmaceutical Sciences, 18th Ed., 1990, Mack Publishing Co., Easton, Pa. (TOC).
Reyes et al., Apr. 2020, Brown Seaweed Fucoidan in Cancer: Implications in Metastasis and Drug Resistance. Mar Drugs. 18(5):232.
Roda et al., 2020, Novel Medicinal Mushroom Blend as a Promising Supplement in Integrative Oncology: A Multi-Tiered Study using 4T1 Triple-Negative Mouse Breast Cancer Model. International Journal of Molecular Sciences. 21(10):3479.
Rossi et al. 2018, B-glucans from Grifola frondosa and Ganoderma lucidum in breast cancer: an example of complementary and integrative medicine. Oncotarget. 9(37):24837-24856.
Rowan et al., 2003, Immunomodulatory activities of mushroom glucans and polysaccharide-protein complexes in animals and humans (a review). Int J Med Mushrooms. 5:95-110.
Saitoh et al., 2009, Fucoidan-Vitamin C complex suppresses tumor invasion through the basement membrane, with scarce injuries to normal or tumor cells, via decreases in oxidative stress and matrix metalloproteinases. Int J Oncol. 35(5):1183-1189.
Saitsu et al., 2019, Improvement of cognitive functions by oral intake of Hericium erinaceus. Biomed Res. 40(4):125-131.
Sanjeewa et al., 2017, The potential of brown-algae polysaccharides for the development of anticancer agents: An update on anticancer effects reported for fucoidan and laminaran. Carbohydr Polym. 177:451-459.

(56) References Cited

OTHER PUBLICATIONS

Schauss et al., 2006, Antioxidant capacity and other bioactivities of the freeze-dried Amazonian palm berry, *Euterpe oleraceae mart.* (acai). J. Agric. Food Chem., 54(22):8604-8610.

Shedden et al., 2001, Efficacy and tolerability of timolol maleate ophthalmic Gel-forming solutino versus timolol ophthalmic solution in adults with open-angle glaucoma or ocular hypertension: a six-month, double-masked, multicenter study, Clin. Ther., 23(3):440-450.

Shin et al., 2022, Lucidumol A, Purified Directly from Ganoderma lucidum, Exhibits Anticancer Effect and Cellular Inflammatory Response in Colorectal Cancer, Evidence-Based Complementary and Alternative Medicine, vol. 2022, Article ID 7404493, 9 pp.

Shirahata et al., 2013, Fucoidan extract enhances the anti-cancer activity of chemotherapeutic agents in breast cancer cells. BMC Proceedings, 7(Suppl6):P70.

Stamets et al., 2018, Extracts of Polypore Mushroom Mycelia Reduce Viruses in Honey Bees. Scientific Reports. 8:13936.

Su et al., 2022, Management of Combined Therapy (Ceritinib, A. cinnamomea, G. lucidum, and Photobiomodulation) in Advanced Non-Small-Cell Lung Cancer: A Case Report. Life, 12(6):862.

Suarez-Arroyo et al., 2016, Ganoderma lucidum Combined with the EGFR Tyrosine Kinase Inhibitor, Erlotinib Synergize to Reduce Inflammatory Breast Cancer Progression. J Cancer. 7(5):500-511.

Suarez-Arroyo et al., Jul. 28, 2017, *Ganoderma* spp.: A Promising Adjuvant Treatment for Breast Cancer. Medicines (Basel). 4(1):15.

Sullivan et al., 2006, Medicinal mushrooms and cancer therapy. Translating a traditional practice into Western medicine. Perspect Biol Med 49:159-170.

Teas et al., Jun. 2012, Dietary algae and HIV/AIDS: proof of concept clinical data. J Appl Phycol. 24(3):575-582.

Thakur et al., 2017, The natural compound fucoidan from New Zealand Undaria pinnatifida synergizes with the ERBB inhibitor lapatinib enhancing melanoma growth inhibition. Oncotarget. 8(11):17887-17896.

Thompson et al., Jul. 2004, Antiviral activity of Undaria pinnatifida against herpes simplex virus. Phytother Res. 18(7):551-555.

Tripodi et al., 2022, Anti-Aging and Neuroprotective Properties of Grifola frondosa and Hericium erinaceus Extracts. Nutrients. 14:4368.

Van Weelden et al., Jan. 2019, Fucoidan Structure and Activity in Relation to Anti-Cancer Mechanisms. Mar Drugs. 17(1):32.

Verma, 2022, Cordycepin: a bioactive metabolite of Cordyceps militaris and polyadenylation inhibitor with therapeutic potential against COVID-19, Journal of Biomolecular Structure and Dynamics, 40(8):3745-3752.

Vishchuk et al., 2011, Sulfated polysaccharides from brown seaweeds *Saccharina japonica* and *Undaria pinnatifida*: isolation, structural characteristics, and antitumor activity. Carbohydr Res. 346(17):2769-2776.

Wang et al., 2014, Extracts from New Zealand Undaria pinnatifida Containing Fucoxanthin as Potential Functional Biomaterials against Cancer in Vitro. J. Funct. Biomater. 5:29-42.

Wasser, 2010, Medicinal mushroom science: history, current status, future trends, and unsolved problems. Int J Med Mushrooms. 12(1):1-16.

Wei et al., Jun. 14, 2022, Cordycepin Inhibits Triple-Negative Breast Cancer Cell Migration and Invasion by Regulating EMT-TFs SLUG, TWIST1, SNAIL1, and ZEB1. Front Oncol. 12:898583.

Wijesekara et al., 2011, Biological activities and potential health benefits of sulfated polysaccharides derived from marine algae. Carbohydr. Polym. 84:14-21.

Wozniak et al., Mar. 2015, Anti-HSV1 activity of brown algal polysaccharides and possible relevance to the treatment of Alzheimer's disease. Int J Biol Macromol. 74:530-540.

Wu et al., Jan. 21, 2015, Preclinical trials for prevention of tumor progression of hepatocellular carcinoma by LZ-8 targeting c-Met dependent and independent pathways. PLoS One. 10(1):e0114495.

Xu et al., 2022, Lucidenic acid A inhibits the binding of hACE2 receptor with spike protein to prevent SARS-CoV-2 invasion, Food and Chemical Toxicology, 169:113438.

Xu et al., Apr. 2020, Fucoidan suppresses the gastric cancer cell malignant phenotype and production of TGF-ß1 via CLEC-2. Glycobiology. 30(5):301-311.

Yadav et al., 2020, A Mechanistic Review on Medicinal Mushrooms-Derived Bioactive Compounds: Potential Mycotherapy Candidates for Alleviating Neurological Disorders. Planta Med. 86(16):1161-1175.

Yadav et al., 2022, Therapeutic Applications of Fucoidans and their Potential to Act Against COVID-19, Current Pharmaceutical Design, XXXX, XX, 1-6.

Yang et al., 2008, Effects of molecular weight and hydrolysis conditions on anticancer activity of fucoidans from sporophyll of Undaria pinnatifida. Int. J. Biol. Macromol. 43:433-437.

Yang et al., Jun. 2016, Fucoidan inhibits lymphangiogenesis by downregulating the expression of VEGFR3 and PROX1 in human lymphatic endothelial cells. Oncotarget. 7(25):38025-38035.

Yanshree et al., 2022, The Monkey Head Mushroom and Memory Enhancement in Alzheimer's Disease. Cells. 11:2284.

Yim et al., 2021, Inhibition of SARS-CoV-2 Virus Entry by the Crude Polysaccharides of Seaweeds and Abalone Viscera In Vitro. Mar. Drugs 19:219.

Zhang et al., 2007, Antitumor polysaccharides from mushrooms: a review on their isolation, structural characteristics and antitumor activity. Trends Food Sci Technol. 18:4-19.

Zhang et al., 2014, Structure-activity relationship of the pro-and anticoagulant effects of Fucus vesiculosus fucoidan. Thromb. Haemos. 111:429-437.

Zhang et al., 2017, Ganoderma lucidum (Reishi) suppresses proliferation and migration of breast cancer cells via inhibiting Wnt/β-catenin signaling. Biochem Biophys Res Commun. 488(4):679-684.

Zhang et al., 2017, Grifola frondosa polysaccharides induce breast cancer cell apoptosis via the mitochondrial-dependent apoptotic pathway. Int J Mol Med. 40(4):1089-1095.

Zhang et al., 2019, Ganoderma lucidum Exerts an Anticancer Effect on Human Osteosarcoma Cells via Suppressing the Wnt/β-Catenin Signaling Pathway. Integr Cancer Ther. 18:1-11.

Zhang et al., 2022, Cordycepin inhibits colon cancer proliferation by suppressing MYC expression. BMC Pharmacol Toxicol. 23(1):12.

Zhang et al., 2022, Medicinal Fungi with Antiviral Effect. Molecules. 27(14):4457.

Zhao et al., 2016, Structural characterization and antiviral activity of a novel heteropolysaccharide isolated from Grifola frondosa against enterovirus 71. Carbohydr Polym. 144:382-389.

Zhao et al., 2017, Synergistic Apoptotic Effect of D-Fraction From Grifola frondosa and Vitamin C on Hepatocellular Carcinoma SMMC-7721 Cells. Integr Cancer Ther. 16(2):205-214.

Zhao et al., Nov. 15, 2021, Antitumor activities of Grifola frondosa (Maitake) polysaccharide: A meta-analysis based on preclinical evidence and quality assessment. J Ethnopharmacol. 280:114395.

Zhao et al., Sep. 2017, The induction of apoptosis and autophagy in human hepatoma SMMC-7721 cells by combined treatment with vitamin C and polysaccharides extracted from Grifola frondosa. Apoptosis. 22:1461-1472.

Zhong et al., 2022, Ganoderma lucidum polysaccharide inhibits the proliferation of leukemic cells through apoptosis. Acta Biochim Pol. 69(3):639-645.

Zhou et al., 2022, Cordycepin inhibits the proliferation and progression of NPC by targeting the MAPK/ERK and β-catenin pathways. Oncol Lett. 23(1):20.

Zhu et al., 2013, Fucoidan inhibits the growth of hepatocellular carcinoma independent of angiogenesis. Evid. Based Complement. Altern. Med. 2013:692549, 7 pp.

Zhu et al., 2019, Improved antitumor activity of cisplatin combined with Ganoderma lucidum polysaccharides in U14 cervical carcinoma-bearing mice. Kaohsiung J Med Sci. 35:222-229.

He et al., 2019, Fucoidan Promotes Apoptosis and Inhibits EMT of Breast Cancer Cells. Biol Pharm Bull. 42(3):442-447.

Mordenti et al., Intraocular pharmacokinetics and safety of a humanized monoclonal antibody in rabbits afeter intravitreal administration of a solution or a PLGA microsphere formulation, Toxicol. Sci., 52(1):101-106, 1999.

Phan et al., 2022, Ganoderma microsporum immunomodulatory protein acts as a multifunctional broad-spectrum antiviral against

(56) References Cited

OTHER PUBLICATIONS

SARS-CoV-2 by interfering virus binding to the host cells and spike-mediated cell fusion. Biomedicine & Pharmacotheraov. 155:133766.

* cited by examiner

METHODS OF INHIBITING CANCER GROWTH AND INHIBITING VIRAL INFECTIONS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

This application is a continuation of Int. App. No. PCT/US2024/015624, filed Feb. 13, 2024, which claims priority to U.S. Provisional Patent Application No. 63/485,452, filed Feb. 16, 2023, both of which are hereby incorporated by reference in their entireties.

BACKGROUND

The present disclosure relates generally to the field of pharmaceuticals and herbal supplements. More particularly, the present disclosure relates to combinations of herbal and other chemical ingredients useful in inhibiting cancer growth and in inhibiting viral attachment. In particular, the disclosure relates to methods and compositions for inhibiting viral attachment and for reducing viral load in an individual, and to methods and compositions for inhibiting cancer growth and for treating cancer in an individual.

SUMMARY

Provided herein, in certain aspects, are compositions and methods for inhibiting cancer growth and inhibiting viral infections.

Accordingly, some embodiments provided herein relate to methods of inhibiting attachment of enveloped viruses in an individual. In embodiments, the method includes administering to the individual a composition including effective amounts of *Laminaria japonica, Undaria pinnatifida, Ganoderma lucidum, Cordyceps sinensis*, and *Hericium erinaceus*. In some embodiments, the method further includes identifying an individual infected with a virus or exposed to a virus. In some embodiments, administering includes daily administration. In some embodiments, the composition is provided in the form of capsules or tablets. In some embodiments, administering includes oral administration.

In some embodiments, the composition further includes an effective amount of *Palmaria palmata*. In some embodiments, the composition includes about 300 mg of *Laminaria japonica*, about 250 mg of *Undaria pinnatifida*, about 250 mg of *Palmaria palmata*, about 250 mg of *Fucus vesiculosus*, about 250 mg of *Grifola frondosa*, about 300 mg of *Ganoderma lucidum*, about 250 mg of *Hericium erinaceus*, about 250 mg of *Cordyceps sinensis*, and about 200 mg of *Euterpe oleracea*.

In embodiments, the virus is adeno-associated virus, dengue virus, ebolavirus, echovirus, encephalomyocarditis virus, Epstein-Barr virus, GB virus C/hepatitis G virus, hepatitis A virus, hepatitis B virus, hepatitis C virus, hepatitis delta virus, hepatitis E virus, human coronavirus, human cytomegalovirus, human enterovirus (68, 70), human herpesvirus 1, human herpesvirus 2, human herpesvirus 6, human herpesvirus 7, human herpesvirus 8, human immunodeficiency virus (HIV), human papillomavirus 1, human papillomavirus (16, 18), human papillomavirus 2, human parainfluenza, human parvovirus B19, human respiratory syncytial virus, human rhinovirus, human SARS coronavirus, influenza A virus, influenza B virus, influenza C virus, measles virus, MERS coronavirus, molluscum contagiosum virus, monkeypox virus, mumps virus, poliovirus, rosavirus A, rotavirus A, rotavirus B, rotavirus C, rubella virus, SARS coronavirus 2, vaccinia virus, vesicular stomatitis virus, West Nile virus, or Zika virus.

In another aspect, provided herein are methods of reducing viral load in an individual. In some embodiments, the method includes identifying an individual having an increased viral load and administering to the individual a composition including effective amounts of *Laminaria japonica, Undaria pinnatifida, Ganoderma lucidum, Cordyceps sinensis*, and *Hericium erinaceus*. In some embodiments, administering includes daily administration. In some embodiments, the composition is provided in the form of capsules or tablets. In some embodiments, administering includes oral administration.

In some embodiments, the composition further includes an effective amount of *Palmaria palmata*. In some embodiments, the composition includes about 300 mg of *Laminaria japonica*, about 250 mg of *Undaria pinnatifida*, about 250 mg of *Palmaria palmata*, about 250 mg of *Fucus vesiculosus*, about 250 mg of *Grifola frondosa*, about 300 mg of *Ganoderma lucidum*, about 250 mg of *Hericium erinaceus*, about 250 mg of *Cordyceps sinensis*, and about 200 mg of *Euterpe oleracea*.

In some embodiments, the virus is adeno-associated virus, dengue virus, ebolavirus, echovirus, encephalomyocarditis virus, Epstein-Barr virus, GB virus C/hepatitis G virus, hepatitis A virus, hepatitis B virus, hepatitis C virus, hepatitis delta virus, hepatitis E virus, human coronavirus, human cytomegalovirus, human enterovirus (68, 70), human herpesvirus 1, human herpesvirus 2, human herpesvirus 6, human herpesvirus 7, human herpesvirus 8, human immunodeficiency virus (HIV), human papillomavirus 1, human papillomavirus (16, 18), human papillomavirus 2, human parainfluenza, human parvovirus B19, human respiratory syncytial virus, human rhinovirus, human SARS coronavirus, influenza A virus, influenza B virus, influenza C virus, measles virus, MERS coronavirus, molluscum contagiosum virus, monkeypox virus, mumps virus, poliovirus, rosavirus A, rotavirus A, rotavirus B, rotavirus C, rubella virus, SARS coronavirus 2, vaccinia virus, vesicular stomatitis virus, West Nile virus, or Zika virus.

In another aspect, provided herein are methods of inhibiting cancer growth in an individual. In some embodiments, the method includes administering to the individual a composition comprising effective amounts of *Laminaria japonica, Undaria pinnatifida, Grifola frondosa, Ganoderma lucidum*, and *Hericium erinaceus*. In some embodiments, the method further includes identifying an individual having a cancer or at risk of having a cancer.

In some embodiments, administering includes daily administration. In some embodiments, the composition is provided in the form of capsules or tablets. In some embodiments, administering includes oral administration.

In some embodiments, the composition further includes an effective amount of *Palmaria palmata*. In some embodiments, the composition includes about 250 mg of *Palmaria palmata*. In some embodiments, the composition includes about 250 mg of *Hericium erinaceus*.

In some embodiments, the composition includes about 300 mg of *Laminaria japonica*, about 250 mg of *Undaria pinnatifida*, about 250 mg of *Palmaria palmata*, about 250 mg of *Fucus vesiculosus*, about 250 mg of *Grifola frondosa*, about 300 mg of *Ganoderma lucidum*, about 250 mg of

*Hericium erinaceus*, about 250 mg of *Cordyceps sinensis*, and about 200 mg of *Euterpe oleracea*.

In some embodiments, the cancer is acute lymphoblastic leukemia, acute monocytic leukemia, acute myeloid leukemia, acute promyelocytic leukemia, adenocarcinoma, adult T-cell leukemia, astrocytoma, bladder cancer, bone cancer, brain cancer, breast cancer, Burkitt's lymphoma, carcinoma, cervical cancer, chronic lymphocytic leukemia, chronic myelogenous leukemia, colon cancer, colorectal cancer, endometrial cancer, glioblastoma multiforme, glioma, hepatocellular carcinoma, Hodgkin's lymphoma, inflammatory breast cancer, kidney cancer, leukemia, lung cancer, lymphoma, malignant mesothelioma, medulloblastoma, melanoma, multiple myeloma, neuroblastoma, non-Hodgkin lymphoma, non-small cell lung cancer, ovarian cancer, pancreatic cancer, pituitary tumor, prostate cancer, retinoblastoma, skin cancer, small cell lung cancer, squamous cell carcinoma, stomach cancer, T-cell leukemia, T-cell lymphoma, thyroid cancer, or Wilms' tumor.

In another aspect, some embodiments provided herein relate to methods of treating cancer in a subject. In some embodiments, the method includes identifying an individual having a cancer, and administering to the individual a composition comprising effective amounts of *Laminaria japonica*, *Undaria pinnatifida*, *Grifola frondosa*, *Ganoderma lucidum*, and *Hericium erinaceus*.

In some embodiments, administering includes daily administration. In some embodiments, the composition is provided in the form of capsules or tablets. In some embodiments, administering includes oral administration.

In some embodiments, the composition further includes an effective amount of *Palmaria palmata*. In some embodiments, the composition includes about 250 mg of *Palmaria palmata*. In some embodiments, the composition includes about 250 mg of *Hericium erinaceus*. In some embodiments, the composition includes about 300 mg of *Laminaria japonica*, about 250 mg of *Undaria pinnatifida*, about 250 mg of *Palmaria palmata*, about 250 mg of *Fucus vesiculosus*, about 250 mg of *Grifola frondosa*, about 300 mg of *Ganoderma lucidum*, about 250 mg of *Hericium erinaceus*, about 250 mg of *Cordyceps sinensis*, and about 200 mg of *Euterpe oleracea*.

In some embodiments, the cancer is acute lymphoblastic leukemia, acute monocytic leukemia, acute myeloid leukemia, acute promyelocytic leukemia, adenocarcinoma, adult T-cell leukemia, astrocytoma, bladder cancer, bone cancer, brain cancer, breast cancer, Burkitt's lymphoma, carcinoma, cervical cancer, chronic lymphocytic leukemia, chronic myelogenous leukemia, colon cancer, colorectal cancer, endometrial cancer, glioblastoma multiforme, glioma, hepatocellular carcinoma, Hodgkin's lymphoma, inflammatory breast cancer, kidney cancer, leukemia, lung cancer, lymphoma, malignant mesothelioma, medulloblastoma, melanoma, multiple myeloma, neuroblastoma, non-Hodgkin lymphoma, non-small cell lung cancer, ovarian cancer, pancreatic cancer, pituitary tumor, prostate cancer, retinoblastoma, skin cancer, small cell lung cancer, squamous cell carcinoma, stomach cancer, T-cell leukemia, T-cell lymphoma, thyroid cancer, or Wilms' tumor.

In another aspect, some embodiments provided herein relate to compositions for use in treatment of cancer. In some embodiments, the composition includes about 300 mg of *Laminaria japonica*, about 250 mg of *Undaria pinnatifida*, about 250 mg of *Palmaria palmata*, about 250 mg of *Fucus vesiculosus*, about 250 mg of *Grifola frondosa*, about 300 mg of *Ganoderma lucidum*, about 250 mg of *Hericium erinaceus*, about 250 mg of *Cordyceps sinensis*, and about 200 mg of *Euterpe oleracea*.

In some embodiments, the cancer is acute lymphoblastic leukemia, acute monocytic leukemia, acute myeloid leukemia, acute promyelocytic leukemia, adenocarcinoma, adult T-cell leukemia, astrocytoma, bladder cancer, bone cancer, brain cancer, breast cancer, Burkitt's lymphoma, carcinoma, cervical cancer, chronic lymphocytic leukemia, chronic myelogenous leukemia, colon cancer, colorectal cancer, endometrial cancer, glioblastoma multiforme, glioma, hepatocellular carcinoma, Hodgkin's lymphoma, inflammatory breast cancer, kidney cancer, leukemia, lung cancer, lymphoma, malignant mesothelioma, medulloblastoma, melanoma, multiple myeloma, neuroblastoma, non-Hodgkin lymphoma, non-small cell lung cancer, ovarian cancer, pancreatic cancer, pituitary tumor, prostate cancer, retinoblastoma, skin cancer, small cell lung cancer, squamous cell carcinoma, stomach cancer, T-cell leukemia, T-cell lymphoma, thyroid cancer, or Wilms' tumor.

BRIEF DESCRIPTION OF THE DRAWINGS

The foregoing and other features of the present disclosure will become more fully apparent from the following description, taken in conjunction with the accompanying drawings. Understanding that these drawings depict only some embodiments in accordance with the disclosure and are therefore, not to be considered limiting of its scope, the disclosure will be described with additional specificity and detail through use of the accompanying drawings.

DETAILED DESCRIPTION

Figure 1A:
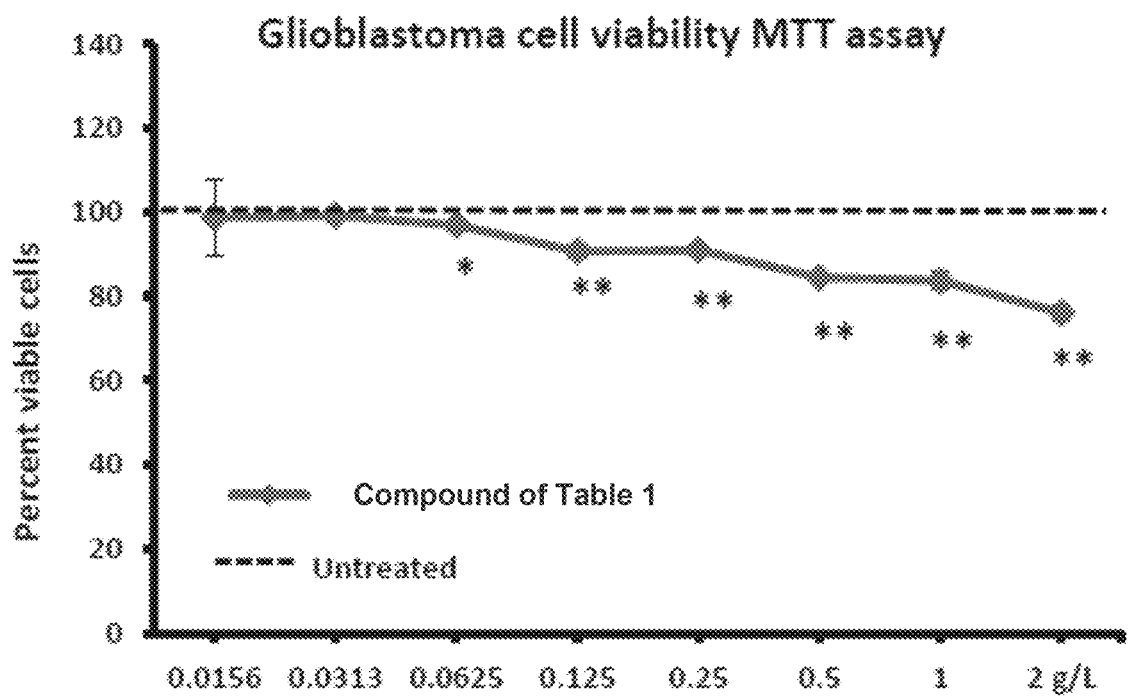
FIG. 1A is a graph showing results of an MTT screening assay of glioblastoma cell viability.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the drawings, can be arranged, substituted, combined, separated, and designed in a wide variety of different configurations, all of which are explicitly contemplated herein.

As summarized herein, aspects of compositions and methods for inhibiting viral attachment, reducing viral load, inhibiting cancer growth, and treating cancer by the administration of compounds of the present disclosure are provided herein.

It is to be understood that this disclosure is not limited to particular embodiments described, as such may, of course, vary. It is also to be understood that the terminology used herein is for the purpose of describing particular embodiments only, and is not intended to be limiting.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Unless defined otherwise, technical and scientific terms used herein have the same meaning as commonly understood by one of ordinary skill in the art to which the present disclosure belongs. For purposes of the present disclosure, the following terms are defined below.

"Inhibit," "inhibiting," and "inhibition" and/or "reduce," "reducing," and "reduction" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90; 100%, or any amount of reduction in between the specifically recited percentages, as compared to native or control levels.

A "subject" or "individual," as used herein, includes any animal that exhibits a symptom, or is at risk for exhibiting a symptom, of one or more cancers or viruses, or disease or disorder associated thereto. Suitable subjects ("patients") include laboratory animals (such as mouse, rat, rabbit, or guinea pig), farm animals, and domestic animals or pets (such as a cat or dog). Non-human primates and, preferably, human patients, are included.

"Viral load" as used herein, refers to a numerical expression of the quantity of virus in a given volume of fluid, including biological and environmental specimens. Viral load is also known as viral burden. Viral load may be measured using body fluids such as sputum and blood plasma. Viral load is often expressed as viral particles, (virions) or infectious particles per mL depending on the type of assay. A higher viral burden, titer, or viral load often correlates with the severity of an active viral infection. The quantity of virus per mL can be calculated by estimating the live amount of virus in an involved fluid. For example, it can be given in RNA copies per milliliter of blood plasma. Tests for measurement of viral load include nucleic acid amplification based tests and non-nucleic acid based tests. Tracking viral load may be used to monitor therapy during chronic viral infections, and in immunocompromised patients such as those recovering from bone marrow or solid organ transplantation. An undetectable viral load does not implicate a lack of infection, as the concentration of virus particles may be below the limit of detection (LOD).

Historically, 47% of cancer drugs approved on the market were originally from a natural origin, and recent research has highlighted more effective and efficient methods than our classical synthetic methods.[1] Reviewing these medical frameworks, demographic data across countries, and detailed statistical analysis of publicly available data, the present application describes formulations that have significant properties to integrate with traditional cancer therapy to help prevent, mitigate, and/or extend the life of cancer diagnosed patients. Such compositions also have activity in reducing viral load and preventing or inhibiting attachment of an enveloped virus in an individual.

In some embodiments, compositions disclosed herein include key polysaccharides such as fucoidans (from specific seaweed species), β-glucans (from specific mushroom species), antioxidant properties (from the specific fruit, *Euterpe oleracea*), and a base multivitamin panel that appears to have dramatic anticancer properties.

Some embodiments of compositions disclosed herein include seaweeds. Seaweeds (with species from brown and red seaweeds such as *Laminaria japonica, Undaria pinnatifida, Fucus vesiculosus*, and *Palmaria* palmita) and their unique related compounds (such as fucoidan, carrageenan, alginates, fucoxanthin and others) have been shown to have activity against many types of cancers,[2-19] including breast cancer[20-22], lung cancer[23], cholangiocarcinoma[24], gastric carcinoma[25], head and neck squamous cell carcinoma[26], HSC-3 oral squamous cell carcinoma[27], fibrosarcoma[28], melanoma[29], prostate cancer[30], and ovarian cancer[31]. Seaweeds and their related compounds have also shown activity against many types of enveloped viruses[12,32], including BVDV (Bovine viral diarrhea virus) 33, coronavirus (including COVID-19)[34-39], influenza[39,40], human immunodeficiency virus (HIV)[39,41-43], hepatitis B virus (HBV)[44], herpes simplex virus (HSV-1)[45-48], and measles[49].

Some species of seaweed include a compound known as fucoidan. Fucoidan has been used in Traditional Chinese Medicine (TCM) for millennia[50]. Fucoidan shows a wide range of biological activities including anticoagulant, anti-inflammatory[51], antidiabetic[52], procoagulant[53], anticancer[54], and antiviral activities[55]. It has low toxicity[56], good biocompatibility[57], and encouraging results in preclinical and sporadic early-stage clinical trials[58,59]. Moreover, it appears to complement and enhance traditional chemotherapy protocols[29,60].

Some embodiments of compositions disclosed herein include mushrooms. Mushrooms (with species such as *Ganoderma lucidum, Grifola frondosa, Cordyceps sinensis*, and *Hericium erinaceus*) and their unique related compounds (such as beta-glucans, proteoglycans, terpenoids and others) have been shown to have activity against many kinds of cancer[61-67], including breast cancer[68-78], cervical cancer[79], cholangiocarcinoma[80], colon cancer[81-84], hepatocellular carcinoma[85-87], laryngeal and pharyngeal cancers[88], leukemia[89], lung cancer[90-93], melanoma[94], nasopharyngeal carcinoma[95], neuroglioma[96], nose and throat (oral squamous cell carcinomas)[97], osteosarcoma[98], ovarian cancer[99], and pancreatic cancer[100]. These mushrooms and their related compounds have also shown activity against many types of enveloped viruses[101,102], such as coronavirus (including COVID-19)[101-104], deformed wing virus (DWV) and *Varroa destructor* virus-1 (VDV1)[105], enterovirus-17[106], influenza[107], herpes simplex virus[107], and human immunodeficiency virus (HIV)[108].

Some species of mushrooms include beta-glucans. Beta glucans (β-glucans) have also been used in TCM, and have shown antitumor, immunomodulating, antioxidant, radical scavenging, cardiovascular, anti-hypercholesterolemia, antiviral, antibacterial, antiparasitic, antifungal, detoxification, hepatoprotective, and antidiabetic effects, and are complementary to traditional chemotherapy protocols.[109-118] Lion's mane (*Hericium erinaceus*) and maitake (*Grifola frondosa*) have also shown improvement of cognitive function and memory enhancement related to Alzheimer's disease.[119-121]

Some embodiments disclosed herein include acai (*Euterpe oleracea*). Antioxidant plants such as acai berry its unique related compounds (such as polyphenols, anthocyanins, proanthocyanidin and others) have been shown to have activity against multiple types of cancer[122], including breast cancer[123-124], melanoma[125], and prostate cancer[126]. Acai and its related compounds have also shown activity against enveloped viruses such as coronavirus (including COVID-19)[127] and human immunodeficiency virus (HIV)[128].

Acai has dramatic antioxidant capability which seems to suggest supporting cell health and vitality. This support is shown by what is known as the oxygen radical absorbance capacity, or ORAC. It measures both the degree and speed with which a certain food inhibits the action of an oxidizing agent, then integrates these two measurements into a single value, producing an accurate assessment of different types of antioxidants of different strengths[129]. Acai is one of the most potent antioxidants available[130] and protects cells from age-related oxidative stress[131].

Some embodiments disclosed herein include vitamins such as vitamin A, vitamin C, calcium, vitamin D3, vitamin E, thiamin, riboflavin, niacin, vitamin B6, folic acid, vitamin B12, pantothenic acid, iron, and lutein. Without being bound to theory, an essential vitamin complement panel may increase activity, specifically, tumor inhibition and suppression (vitamin C & fucoidan[28, 132]; vitamin C and maitake[96, 133, 134, 135]) and increase the absorption of larger polysaccharides like those from reishi and maitake.

In some aspects, provided herein is a method of inhibiting attachment of enveloped viruses in an individual. In another aspect is provided a method of reducing viral load in an individual. In both aspects, in some embodiments, the method includes administering to the individual a composition comprising effective amounts of *Laminaria japonica, Undaria pinnatifida, Ganoderma lucidum, Cordyceps sinensis*, and *Hericium erinaceus*. In some embodiments, the composition further includes an effective amount of *Palmaria palmata*.

In some embodiments, the composition comprises about 150-450 mg of *Laminaria japonica*, about 200-400 mg of *Undaria pinnatifida*, about 200-400 mg of *Palmaria palmata*, about 200-400 mg of *Fucus vesiculosus*, about 200-400 mg of *Grifola frondosa*, about 200-400 mg of *Ganoderma lucidum*, about 200-400 mg of *Hericium erinaceus*, about 200-400 mg of *Cordyceps sinensis*, and about 100-300 mg of *Euterpe oleracea*. In some embodiments, the composition comprises about 300 mg of *Laminaria japonica*, about 250 mg of *Undaria pinnatifida*, about 250 mg of *Palmaria palmata*, about 250 mg of *Fucus vesiculosus*, about 250 mg of *Grifola frondosa*, about 300 mg of *Ganoderma lucidum*, about 250 mg of *Hericium erinaceus*, about 250 mg of *Cordyceps sinensis*, and about 200 mg of *Euterpe oleracea*.

In some embodiments, the method further includes identifying an individual infected with a virus or exposed to a virus. In some embodiments, the method further includes identifying an individual having an increased viral load. In some embodiments, identifying includes self-identification. In some embodiments, identifying an individual infected with a virus or identifying an individual having an increased viral load includes identification through a test such as a nucleic acid amplification test (NAAT, including PCR-based tests) or through an antigen test. In some embodiments, identifying an individual exposed to a virus includes through identified exposure events.

In some embodiments, administering includes daily administration. In some embodiments, administration includes self-administration. In some embodiments, administration is once daily. In some embodiments, administration is twice daily, three times daily, or more. In some embodiments, administering includes oral administration. In some embodiments, the composition is provided in the form of capsules or tablets.

In some embodiments, the virus is adeno-associated virus, dengue virus, ebolavirus, echovirus, encephalomyocarditis virus, Epstein-Barr virus, GB virus C/hepatitis G virus, hepatitis A virus, hepatitis B virus, hepatitis C virus, hepatitis delta virus, hepatitis E virus, human coronavirus, human cytomegalovirus, human enterovirus (68, 70), human herpesvirus 1, human herpesvirus 2, human herpesvirus 6, human herpesvirus 7, human herpesvirus 8, human immunodeficiency virus (HIV), human papillomavirus 1, human papillomavirus (16, 18), human papillomavirus 2, human parainfluenza, human parvovirus B19, human respiratory syncytial virus, human rhinovirus, human SARS coronavirus, influenza A virus, influenza B virus, influenza C virus, measles virus, MERS coronavirus, molluscum contagiosum virus, monkeypox virus, mumps virus, poliovirus, rosavirus A, rotavirus A, rotavirus B, rotavirus C, rubella virus, SARS coronavirus 2, vaccinia virus, vesicular stomatitis virus, West Nile virus, or Zika virus.

Further provided herein are methods of inhibiting cancer growth in an individual and of treating cancer in a subject. In some embodiments, the methods include administering to the individual a composition comprising effective amounts of *Laminaria japonica, Undaria pinnatifida, Grifola frondosa, Ganoderma lucidum*, and *Hericium erinaceus*. In some embodiments, the composition includes about 250 mg of *Hericium erinaceus*.

In some embodiments, the composition further comprises an effective amount of *Palmaria palmata*. In some embodiments, the composition includes about 250 mg of *Palmaria palmata*.

In some embodiments, the composition comprises about 150-450 mg of *Laminaria japonica*, about 200-400 mg of *Undaria pinnatifida*, about 200-400 mg of *Palmaria palmata*, about 200-400 mg of *Fucus vesiculosus*, about 200-400 mg of *Grifola frondosa*, about 200-400 mg of *Ganoderma lucidum*, about 200-400 mg of *Hericium erinaceus*, about 200-400 mg of *Cordyceps sinensis*, and about 100-300 mg of *Euterpe oleracea*. In some embodiments, the composition comprises about 300 mg of *Laminaria japonica*, about 250 mg of *Undaria pinnatifida*, about 250 mg of *Palmaria palmata*, about 250 mg of *Fucus vesiculosus*, about 250 mg of *Grifola frondosa*, about 300 mg of *Ganoderma lucidum*, about 250 mg of *Hericium erinaceus*, about 250 mg of *Cordyceps sinensis*, and about 200 mg of *Euterpe oleracea*.

In some embodiments, the method includes identifying an individual having a cancer or an individual at risk of having a cancer. In some embodiments, identifying includes self-identification. In some embodiments, identifying an individual having a cancer includes diagnosis by any means known in the art, including blood test, urine test, biopsy including tissue biopsy and liquid biopsy, endoscopy, surgery, imaging test such as CT scan, MRI, nuclear scan, bone scan, PET scan, ultrasound, or x-ray. In some embodiments, identifying an individual at risk of having a cancer includes screening (physical examination), genetic test, and assessment of risk factors such as age, personal or family history of cancer, tobacco use, obesity, alcohol use, viral infection such as HPV, exposure to carcinogenic chemicals, and exposure to radiation including UV radiation.

In some embodiments, administering includes daily administration. In some embodiments, administration includes self-administration. In some embodiments, administration is once daily. In some embodiments, administration is twice daily, three times daily, or more. In some embodiments, administering includes oral administration. In some embodiments, the composition is provided in the form of capsules or tablets. In some embodiments, the composition is administered in combination with chemotherapy treatment.

In some embodiments, the cancer is acute lymphoblastic leukemia, acute monocytic leukemia, acute myeloid leukemia, acute promyelocytic leukemia, adenocarcinoma, adult T-cell leukemia, astrocytoma, bladder cancer, bone cancer, brain cancer, breast cancer, Burkitt's lymphoma, carcinoma, cervical cancer, chronic lymphocytic leukemia, chronic myelogenous leukemia, colon cancer, colorectal cancer, endometrial cancer, glioblastoma multiforme, glioma, hepatocellular carcinoma, Hodgkin's lymphoma, inflammatory breast cancer, kidney cancer, leukemia, lung cancer, lymphoma, malignant mesothelioma, medulloblastoma, melanoma, multiple myeloma, neuroblastoma, non-Hodgkin lymphoma, non-small cell lung cancer, ovarian cancer, pancreatic cancer, pituitary tumor, prostate cancer, retinoblastoma, skin cancer, small cell lung cancer, squamous cell carcinoma, stomach cancer, T-cell leukemia, T-cell lymphoma, thyroid cancer, or Wilms' tumor.

In some embodiments, the composition includes *Laminaria japonica*, which may be also referred to as *Saccharina japonica*. In some embodiments, the composition includes an effect amount of *Laminaria japonica*. In some embodiments, the composition comprises between 100-500 mg of *Laminaria japonica*, between 200-400 mg of *Laminaria japonica*, between 250-350 mg of *Laminaria japonica*, between 280-320 mg of *Laminaria japonica*, about 300 mg of *Laminaria japonica*, or a value within any of the aforementioned ranges, or a range constructed from any of the aforementioned values.

In some embodiments, the composition includes *Undaria pinnatifida*. In some embodiments, the composition includes an effect amount of *Undaria pinnatifida*. In some embodiments, the composition comprises between 100-500 mg of *Undaria pinnatifida*, between 200-350 mg of *Undaria pinnatifida*, between 250-350 mg of *Undaria pinnatifida*, about 250 mg of *Undaria pinnatifida*, about 300 mg of *Undaria pinnatifida*, or a value within any of the aforementioned ranges, or a range constructed from any of the aforementioned values.

In some embodiments, the composition includes *Fucus vesiculosus*. In some embodiments, the composition includes an effect amount of *Fucus vesiculosus*. In some embodiments, the composition comprises between 100-400 mg of *Fucus vesiculosus*, between 200-350 mg of *Fucus vesiculosus*, between 250-350 mg of *Fucus vesiculosus*, about 250 mg of *Fucus vesiculosus*, about 300 mg of *Fucus vesiculosus*, or a value within any of the aforementioned ranges, or a range constructed from any of the aforementioned values.

In some embodiments, the composition includes *Grifola frondosa*. In some embodiments, the composition includes an effect amount of *Grifola frondosa*. In some embodiments, the composition comprises between 100-400 mg of *Grifola frondosa*, between 200-350 mg of *Grifola frondosa*, between 250-350 mg of *Grifola frondosa*, about 250 mg of *Grifola frondosa*, about 300 mg of *Grifola frondosa*, or a value within any of the aforementioned ranges, or a range constructed from any of the aforementioned values.

In some embodiments, the composition includes *Ganoderma lucidum*. In some embodiments, the composition includes an effect amount of *Ganoderma lucidum*. In some embodiments, the composition comprises between 100-400 mg of *Ganoderma lucidum*, between 200-350 mg of *Ganoderma lucidum*, between 250-350 mg of *Ganoderma lucidum*, about 250 mg of *Ganoderma lucidum*, about 300 mg of *Ganoderma lucidum*, or a value within any of the aforementioned ranges, or a range constructed from any of the aforementioned values.

In some embodiments, the composition includes *Cordyceps sinensis*. In some embodiments, the composition includes an effect amount of *Cordyceps sinensis*. In some embodiments, the composition comprises between 100-400 mg of *Cordyceps sinensis*, between 200-350 mg of *Cordyceps sinensis*, between 250-350 mg of *Cordyceps sinensis*, about 250 mg of *Cordyceps sinensis*, about 300 mg of *Cordyceps sinensis*, or a value within any of the aforementioned ranges, or a range constructed from any of the aforementioned values.

In some embodiments, the composition includes *Hericium erinaceus*. In some embodiments, the composition includes an effect amount of *Hericium erinaceus*. In some embodiments, the composition comprises between 100-400 mg of *Hericium erinaceus*, between 200-350 mg of *Hericium erinaceus*, between 250-350 mg of *Hericium erinaceus*, about 250 mg of *Hericium erinaceus*, about 300 mg of *Hericium erinaceus*, or a value within any of the aforementioned ranges, or a range constructed from any of the aforementioned values.

In some embodiments, the composition includes *Palmaria palmata*. In some embodiments, the composition includes an effect amount of *Palmaria palmata*. In some embodiments, the composition comprises between 100-400 mg of *Palmaria palmata*, between 200-350 mg of *Palmaria palmata*, between 250-350 mg of *Palmaria palmata*, about 250 mg of *Palmaria palmata*, about 300 mg of *Palmaria palmata*, or a value within any of the aforementioned ranges, or a range constructed from any of the aforementioned values.

In some embodiments, the composition includes *Euterpe oleracea*. In some embodiments, the composition includes an effect amount of *Euterpe oleracea*. In some embodiments, the composition comprises between 100-400 mg of *Euterpe oleracea*, between 150-350 mg of *Euterpe oleracea*, between 180-280 mg of *Euterpe oleracea*, about 200 mg of *Euterpe oleracea*, about 250 mg of *Euterpe oleracea*, or a value within any of the aforementioned ranges, or a range constructed from any of the aforementioned values.

In some embodiments, the composition includes vitamin A. In some embodiments, the vitamin A is included as vitamin A acetate. In some embodiments, the composition includes an effective amount of vitamin A. In some embodiments, the composition comprises between 10-10,000 IU of vitamin A, between 3,000-7,000 IU of vitamin A, between 4,000-6,000 IU of vitamin A, between 4,500-5,500 IU of vitamin A, about 5,000 IU of vitamin A, or a value within any of the aforementioned ranges, or a range constructed from any of the aforementioned values.

In some embodiments, the composition includes vitamin C. In some embodiments, the vitamin C is included as ascorbic acid. In some embodiments, the composition includes an effective amount of vitamin C. In some embodiments, the composition comprises between 5-200 mg of vitamin C, between 20-120 mg of vitamin C, between 30-90 mg of vitamin C, between 40-80 mg of vitamin C, about 60 mg of vitamin C, or a value within any of the aforementioned ranges, or a range constructed from any of the aforementioned values.

In some embodiments, the composition includes vitamin D. In some embodiments, the vitamin D is vitamin D3. In some embodiments, the vitamin D is included as cholecalciferol. In some embodiments, the composition includes an effective amount of vitamin D. In some embodiments, the composition comprises between 10-2,000 IU of vitamin D, between 100-1,000 IU of vitamin D, between 200-800 IU of vitamin D, between 300-700 IU of vitamin D, about 400 IU of vitamin D, or a value within any of the aforementioned ranges, or a range constructed from any of the aforementioned values.

In some embodiments, the composition includes vitamin E. In some embodiments, the vitamin E is included as DL-alpha tocopheryl acetate. In some embodiments, the composition includes an effective amount of vitamin E. In some embodiments, the composition comprises between 5-200 IU of vitamin E, between 10-100 IU of vitamin E, between 20-80 IU of vitamin E, between 25-50 IU of vitamin E, about 30 IU of vitamin E, or a value within any of the aforementioned ranges, or a range constructed from any of the aforementioned values.

In some embodiments, the composition includes thiamin (vitamin B1). In some embodiments, the thiamin is included as thiamin HCl. In some embodiments, the composition includes an effective amount of thiamin. In some embodiments, the composition comprises between 0.5-3.0 mg of thiamin, between 0.8-2.5 mg of thiamin, between 1.0-2.0 mg thiamin, between 1.2-1.8 mg of thiamin, about 1.5 mg of thiamin, or a value within any of the aforementioned ranges, or a range constructed from any of the aforementioned values.

In some embodiments, the composition includes riboflavin (vitamin B2). In some embodiments, the riboflavin is included as sodium riboflavin phosphate. In some embodiments, the composition includes an effective amount of riboflavin. In some embodiments, the composition comprises between 0.5-3.0 mg of riboflavin, between 0.8-2.5 mg of riboflavin, between 1.0-2.0 mg riboflavin, between 1.2-1.8 mg of riboflavin, about 1.7 mg of riboflavin, or a value within any of the aforementioned ranges, or a range constructed from any of the aforementioned values.

In some embodiments, the composition includes niacin. In some embodiments, the niacin is included as nicotinic acid. In some embodiments, the composition includes an effective amount of niacin. In some embodiments, the composition comprises between 1-100 mg of niacin, between 5-80 mg of niacin, between 10-50 mg niacin, between 15-30 mg of niacin, about 20 mg of niacin, or a value within any of the aforementioned ranges, or a range constructed from any of the aforementioned values.

In some embodiments, the composition includes vitamin B6. In some embodiments, the vitamin B6 is included as pyridoxine HCl. In some embodiments, the composition includes an effective amount of vitamin B6. In some embodiments, the composition comprises between 0.1-10 mg of vitamin B6, between 0.5-5 mg of vitamin B6, between 0.8-4 mg vitamin B6, between 1-3 mg of vitamin B6, about 2 mg of vitamin B6, or a value within any of the aforementioned ranges, or a range constructed from any of the aforementioned values.

In some embodiments, the composition includes folic acid. In some embodiments, the composition includes an effective amount of folic acid. In some embodiments, the composition comprises between 10-2,000 mcg of folic acid, between 100-1,000 mcg of folic acid, between 200-800 mcg of folic acid, between 300-700 mcg of folic acid, about 400 mcg of folic acid, or a value within any of the aforementioned ranges, or a range constructed from any of the aforementioned values.

In some embodiments, the composition includes vitamin B12. In some embodiments, the vitamin B12 is included as cyanocobalamin. In some embodiments, the vitamin B12 is included as methylcobalamin (MeCbl). In some embodiments, the composition includes an effective amount of vitamin B12. In some embodiments, the composition comprises between 0.1-20 mcg of vitamin B12, between 2-10 mcg of vitamin B12, between 3-8 mcg vitamin B12, between 4-7 mcg of vitamin B12, about 6 mcg of vitamin B12, or a value within any of the aforementioned ranges, or a range constructed from any of the aforementioned values.

In some embodiments, the composition includes pantothenic acid. In some embodiments, the pantothenic acid is included as d-calcium pantothenate. In some embodiments, the composition includes an effective amount of pantothenic acid. In some embodiments, the composition comprises between 1-50 mg of pantothenic acid, between 3-30 mg of pantothenic acid, between 5-20 mg pantothenic acid, between 7-15 mg of pantothenic acid, about 10 mg of pantothenic acid, or a value within any of the aforementioned ranges, or a range constructed from any of the aforementioned values.

In some embodiments, the composition includes calcium. In some embodiments, the calcium is included as calcium carbonate. In some embodiments, the composition includes an effective amount of calcium. In some embodiments, the composition comprises between 10-100 mg of calcium, between 20-70 mg of calcium, between 30-60 mg calcium, between 40-50 mg of calcium, about 45 mg of calcium, or a value within any of the aforementioned ranges, or a range constructed from any of the aforementioned values.

In some embodiments, the composition includes iron. In some embodiments, the iron is included as ferrous sulfate. In some embodiments, the composition includes an effective amount of iron. In some embodiments, the composition comprises between 1-50 mg of iron, between 3-40 mg of iron, between 5-30 mg iron, between 10-20 mg of iron, about 15 mg of iron, or a value within any of the aforementioned ranges, or a range constructed from any of the aforementioned values.

In some embodiments, the composition includes lutein. In some embodiments, the composition includes an effective amount of lutein. In some embodiments, the composition comprises between 1-50 mg of lutein, between 3-30 mg of lutein, between 5-20 mg lutein, between 7-15 mg of lutein, about 10 mg of lutein, or a value within any of the aforementioned ranges, or a range constructed from any of the aforementioned values.

An exemplary composition for use in the methods presented herein is described below in Table 1.

TABLE 1

| Ingredient | Amount (mg, unless specified otherwise) |
| --- | --- |
| Kombu (*Laminaria japonica*) | 300 |
| Wakame (*Undaria pinnatifida*) | 300 |
| Bladderwrack (*Fucus vesiculosus*) | 250 |
| Maitake (*Grifola frondosa*) | 250 |
| Reishi (*Ganoderma lucidum*) | 300 |
| Cordyceps (*Cordyceps sinensis*) | 300 |
| Acai (*Euterpe oleracea*) | 300 |
| Vitamin A | 5000 IU (international unit) |
| Vitamin C | 60 |
| Vitamin D | 400 IU |
| Vitamin E | 30 IU |
| Thiamin (B1) | 1.5 |
| Riboflavin (B2) | 1.7 |
| Niacin | 20 |
| Vitamin B6 | 2 |

TABLE 1-continued

| Ingredient | Amount (mg, unless specified otherwise) |
|---|---|
| Folic Acid | 400 mcg (microgram) |
| Vitamin B12 | 6 mcg |
| Pantothenic Acid | 10 |
| Calcium | 45 |

A second exemplary composition for use in the methods presented herein is described below in Table 2.

TABLE 2

| Ingredient | Amount (mg, unless specified otherwise) |
|---|---|
| Kombu (*Laminaria japonica*) | 300 |
| Wakame (*Undaria pinnatifida*) | 250 |
| Bladderwrack (*Fucus vesiculosus*) | 250 |
| Dulse (*Palmaria palmata*) | 250 |
| Maitake (*Grifola frondosa*) | 250 |
| Reishi (*Ganoderma lucidum*) | 300 |
| Cordyceps (*Cordyceps sinensis*) | 250 |
| Lion's Mane (*Hericium erinaceus*) | 250 |
| Acai (*Euterpe oleracea*) | 200 |
| Vitamin A | 5000 IU (international unit) |
| Vitamin C | 60 |
| Vitamin D | 400 IU |
| Vitamin E | 30 IU |
| Thiamin (B1) | 1.5 |
| Riboflavin (B2) | 1.7 |
| Niacin | 20 |
| Vitamin B6 | 2 |
| Folic Acid | 400 mcg (microgram) |
| Vitamin B12 | 6 mcg |
| Pantothenic Acid | 10 |
| Calcium | 45 |
| Iron | 15 |
| Lutein | 10 |

Pharmaceutical Compositions

In some embodiments, the active ingredients and mixtures of active ingredients may be used, for example, in pharmaceutical compositions comprising a pharmaceutically acceptable carrier prepared for storage and subsequent administration. Also, some embodiments include use of the above-described active ingredients with a pharmaceutically acceptable carrier or diluent. Acceptable carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes and even flavoring agents may be provided in the pharmaceutical composition. For example, sodium benzoate, ascorbic acid and esters of p-hydroxybenzoic acid may be added as preservatives. In addition, antioxidants and suspending agents may be used.

Compositions of the active ingredients may be formulated and used as tablets, capsules, or elixirs for oral administration; suppositories for rectal administration; sterile solutions, suspensions for injectable administration; patches for transdermal administration, and sub-dermal deposits and the like. Injectables can be prepared. in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. If desired, absorption enhancing preparations (for example, liposomes), may be utilized.

For injection, agents may be formulated in aqueous solutions, preferably in physiologically compatible buffers such as Hanks' solution, Ringer's solution, or physiological saline buffer. For such transmucosal administration, penetrants appropriate to the barrier to be permeated are used in the formulation. Such penetrants are generally known in the art. Use of pharmaceutically acceptable carriers to formulate the ingredients herein disclosed for the practice into dosages suitable for systemic administration is within the scope of the disclosure. With proper choice of carrier and suitable manufacturing practice, the compositions disclosed herein, in particular, those formulated as solutions, may be administered parenterally, such as by intravenous injection. The active ingredients can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a patient to be treated.

Pharmaceutical formulations for parenteral administration include aqueous solutions of the active ingredients in water-soluble form. Additionally, suspensions of the active ingredients may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the ingredients to allow for the preparation of highly concentrated solutions.

Pharmaceutical preparations for oral use can be obtained by combining the active ingredients with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active ingredient doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active ingredient doses. Such formulations can be made using methods known in the art. See, for example, U.S. Pat.

No. 5,733,888 (injectable compositions); U.S. Pat. No. 5,726,181 (poorly water soluble compounds); U.S. Pat. No. 5,707,641 (therapeutically active proteins or peptides); U.S. Pat. No. 5,667,809 (lipophilic agents); U.S. Pat. No. 5,576,012 (solubilizing polymeric agents); U.S. Pat. No. 5,707,615 (anti-viral formulations); U.S. Pat. No. 5,683,676 (particulate medicaments); U.S. Pat. No. 5,654,286 (topical formulations); U.S. Pat. No. 5,688,529 (oral suspensions); U.S. Pat. No. 5,445,829 (extended release formulations); U.S. Pat. No. 5,653,987 (liquid formulations); U.S. Pat. No. 5,641,515 (controlled release formulations) and U.S. Pat. No. 5,601,845 (spheroid formulations); all of which are incorporated herein by reference in their entireties. The pharmaceutical compositions may be manufactured in a manner that is itself known, for example, by means of conventional mixing, dissolving, granulating, dragee-making, levitating, emulsifying, encapsulating, entrapping, or lyophilizing processes.

To formulate the dosage including one or more active ingredients disclosed herein, known surface active agents, excipients, smoothing agents, suspension agents and pharmaceutically acceptable film-forming substances and coating assistants, and the like may be used. Preferably alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents. In addition to the foregoing ingredients, sweeteners, fragrances, colorants, preservatives and the like may be added to the administered formulation of the compound, particularly when the compound is to be administered orally.

Further disclosed herein are various pharmaceutical compositions well known in the pharmaceutical art for uses that include intraocular, intranasal, and intraauricular delivery. Pharmaceutical formulations include aqueous ophthalmic solutions of the active ingredients in water-soluble form, such as eyedrops, or in gellan gum (Shedden et al., Clin. Ther., 23 (3): 440-50 (2001)) or hydrogels (Mayer et al., Ophthalmologica, 210 (2): 101-3 (1996)); ophthalmic ointments; ophthalmic suspensions, such as microparticulates, drug-containing small polymeric particles that are suspended in a liquid carrier medium (Joshi, A., J. Ocul. Pharmacol., 10 (1): 29-45 (1994)), lipid-soluble formulations (Alm et al., Prog. Clin. Biol. Res., 312:447-58 (1989)), and microspheres (Mordenti, Toxicol. Sci., 52 (1): 101-6 (1999)); and ocular inserts. All of the above-mentioned references (and those that appear in the disclosure hereafter), are incorporated herein by reference in their entireties. Such suitable pharmaceutical formulations are most often and preferably formulated to be sterile, isotonic and buffered for stability and comfort. Pharmaceutical compositions may also include drops and sprays often prepared to simulate in many respects nasal secretions to ensure maintenance of normal ciliary action. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the car. Common solvents for such aural formulations include glycerin and water.

The compositions described herein may be administered by either oral or a non-oral pathways. When administered orally, compositions can be administered in capsule, tablet, granule, spray, syrup, or other such form. Compositions also may be brewed, as with a tea, or formed by dissolving a powdered composition into a fluid, typically water, fruit or vegetable juice, or milk. When administered non-orally, it can be administered as an aqueous suspension, an oily preparation or the like or as a drip, suppository, salve, ointment or the like, when administered via injection, subcutaneously, intreperitoneally, intravenously, intramuscularly, or the like. Similarly, it may be administered topically, rectally, or vaginally, as deemed appropriate by those of skill in the art for bringing the ingredients into optimal contact with living tissue.

Agents intended to be administered intracellularly may be administered using techniques well known to those of ordinary skill in the art. For example, such agents may be encapsulated into liposomes, then administered by any of the methods described herein. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. Additionally, due to their hydrophobicity, small organic molecules may be directly administered intracellularly.

In some embodiments, the compositions described herein are formulated into a single pill or tablet. In some embodiments, the pill or tablet has a mass from 10 mg to 4000 mg. In some embodiments, the pill or tablet has a mass from 100 mg to 3500 mg. In some embodiments, the pill or tablet has a mass from 800 mg to 3000 mg. In some embodiments, the pill or tablet has a mass from 1200 mg to 2800 mg.

Methods of Administration

Some embodiments also encompass methods for making and for administering the disclosed compositions. Such disclosed methods include, among others, (a) administration though oral pathways, which administration includes administration in capsule, tablet, granule, spray, syrup, or other such forms; (b) administration through non-oral pathways, which administration includes administration as an aqueous suspension, an oily preparation or the like or as a drip, suppository, salve, ointment or the like; administration via injection, subcutaneously, intraperitoneally, intravenously, intramuscularly, intradermally, or the like; as well as (c) administration topically, (d) administration rectally, or (e) administration vaginally, as deemed appropriate by those of skill in the art for bringing the compound into contact with living tissue; and (f) administration via controlled released formulations, depot formulations, and infusion pump delivery. As further examples of such modes of administration and as further disclosure of modes of administration, disclosed herein are various methods for administration of the disclosed compositions including modes of administration through intraocular, intranasal, and intraauricular pathways.

The pharmaceutically effective amount of the ingredients disclosed herein required as a dose will depend on the route of administration and the physical characteristics of the specific human under consideration. The dose can be tailored to achieve a desired effect, but will depend on such factors as weight, diet, concurrent medication and other factors, which those skilled in the medical arts will recognize.

In practicing the methods, the products or compositions can be used alone or in combination with one another or in combination with other therapeutic or diagnostic agents. These products can be utilized in vivo, ordinarily in a mammal, preferably in a human, or in vitro. In employing them in vivo, the products or compositions can be administered to the mammal in a variety of ways, including parenterally, intravenously, subcutaneously, intramuscularly, colonically, rectally, vaginally, nasally or intraperitoneally, employing a variety of dosage forms. Such methods may also be applied to testing chemical activity in vivo.

As will be readily apparent to one skilled in the art, the useful in vivo dosage to be administered and the particular mode of administration will vary depending upon the age, weight and mammalian species treated, the particular ingredients employed, and the specific use for which these ingredients are employed. The determination of effective dosage levels, that is, the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods. In non-human animal studies, applications of potential products are commenced at higher dosage levels, with dosage being decreased until the desired effect is no longer achieved or adverse side effects disappear.

The dosage of active ingredient(s) may range broadly, depending upon the desired affects and the therapeutic indication. Typically, dosages of active ingredient(s) may be between about 10 microgram/kg and 100 mg/kg body weight, preferably between about 100 microgram/kg and 10 mg/kg body weight. In some embodiments, the dosage of active ingredient(s) may be 1, 2, 3, 4, 5, 6, 7, 8 or 9 mg/kg body weight. Alternatively, dosages may be based and calculated upon the surface area of the patient, as understood by those of skill in the art. In a preferred embodiment, administration is oral on a daily, twice daily, or ad hoc basis.

The exact formulation, route of administration and dosage can be chosen in view of the consumer's condition. See for example, Fingl et al., in The Pharmacological Basis of Therapeutics, 1975, which is incorporated herein by reference in its entirety. The magnitude of an administered dose may vary with the severity of a particular medical or physical condition and the route of administration. The severity of a condition may, for example, be evaluated, in part, by standard prognostic evaluation methods. Further, the dose and perhaps dose frequency, may also vary according to the age, body weight, and response of the individual. A program comparable to that discussed above may be used in veterinary medicine.

A variety of techniques for formulation and administration may be found in Remington's Pharmaceutical Sciences, 18th Ed., Mack Publishing Co., Easton, Pa. (1990), which is incorporated herein by reference in its entirety. Suitable administration routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

The combined active ingredients in the compositions disclosed herein may be orally or non-orally administered to a human patient in the amount of about 0.0007 mg/day to about 7,000 mg/day of the total active ingredients, and more preferably about 0.07 mg/day to about 70 mg/day of the total active ingredients at, one time per day or in other embodiments, over two to about ten times per day. Alternatively, the active ingredients disclosed herein may be administered in the stated amounts continuously by, for example, an intravenous drip. Thus, for a patient weighing 70 kilograms, the preferred daily dose of the total active ingredients would be about 0.0007 mg/kg/day to about 35 mg/kg/day, and more preferable, 0.007 mg/kg/day to about 15 mg/kg/day. Nonetheless, as will be understood by those of skill in the art, in certain situations it may be necessary to administer the active ingredients disclosed herein in amounts that excess, or even far exceed, the above-stated, preferred dosage range to treat effectively and aggressively a desired condition or characteristic.

Ingredients disclosed herein can be evaluated for efficacy and toxicity using known methods. For example, the toxicology of a particular compound or ingredient, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds or ingredients in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition, including the conditions abated by the compounds or ingredients disclosed herein, including obesity. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound or ingredient in humans.

The active ingredients described above may be used alone or in combination with one another, or in combination with other therapeutic or diagnostic agents. These products can be utilized in vivo or in vitro. The useful dosages and the most useful modes of administration will vary depending upon the age and weight of the consumer, the particular ingredients employed, and the specific use for which these ingredients are employed. In some embodiments, the composition described herein is formulated as a tablet. In some embodiments, the composition described herein is formulated as a capsule. In some embodiments, the composition comprises gelatin. In some embodiments, the composition comprises cellulose. In some embodiments, the composition comprises magnesium stearate.

EXAMPLES

Some aspects of the embodiments discussed above are disclosed in further detail in the following examples, which are not in any way intended to limit the scope of the present disclosure. Those in the art will appreciate that many other embodiments also fall within the scope of the disclosure, as it is described herein above and in the claims.

Example 1

The composition described in Table 1 was administered daily to a 24-year-old female subject diagnosed with an ovarian cyst disease, causing multiple ovarian tumors in her life, a left kidney tumor, and irritable bowel syndrome (IBS), linked to these cysts in her abdomen. The subject was also diagnosed as infertile. Administration was oral and the composition was formulated as a capsule. After 5 months of daily administration, the ovarian cyst disease was entirely reduced, left kidney tumor was gone, and irritable bowel syndrome completely cleared. Moreover, upon a routine ultrasound looking for tumors and cysts, the subject was found to be pregnant. The subject has been clear of ovarian cyst disease, kidney tumors, and IBS since taking composition described in Table 1 and currently has two children since beginning taking of the composition stated in Table 1.

Example 2

The composition described in Table 1 was administered daily to a 38-year-old female subject diagnosed with an ovarian tumor on her left side. By month 4 of administration, the subject began to notice a marked increase in energy and no longer felt dramatically fatigued. An MRI revealed no growths or tumors on either of the ovaries, confirmed by the subject's physician. Subsequent MRIs for the next 3 months monitored the subject and found no tumor growth.

Example 3

The composition described in Table 1 was administered daily to a 60-year-old male subject diagnosed with prostate cancer and having elevated prostate specific antigen level (15) and a biopsy Gleason score of 8. The PSA level indicated the probable existence of a prostate cancer and the Gleason score indicated high risk of spreading and mortality. The subject's insurance declined chemoradiation treatment due to his related comorbidities. The composition described in Table 1 was administered to the subject for 4 weeks. At the end of the 4 weeks, a second PSA test resulted in a score of 8. The subject reported feeling more energy and continued to take said composition. After another 4 weeks of taking the composition, a new PSA test resulted in a score of 1. The subject's physician continued to monitor the subject monthly until month 6. At month 6 testing date, a new PSA and Gleason score was taken where they were 1 and 0 (unable to detect), respectively.

Example 4

The composition described in Table 1 was administered daily to a 55-year-old female subject diagnosed with a breast cancer, stage IV. The subject underwent chemotherapy treatment and was beginning to show signs of debilitation, heavy fatigue, and hair loss by her 4th round of treatment. The subject had a 5th and final round of treatment followed by a scan of her breast tissue. Scan showed the cancer was no longer a large set of lumps but multiple smaller ones, indicating a heavy metastasis episode. Subject took the composition described in Table 1 for 2 weeks. At the end of the 2 weeks, the subject felt more energetic and noticed her hair growing back with minor fuzz. The subject's physician remarked that patients do not typically see hair growth post chemo until 2 months after chemotherapy. The subject continued to experience a marked increase in her energy despite the chemotherapy treatment and scans showing she still had metastatic tumors. The subject's physician advised the subject to keep taking composition described in Table 1. The subject continued to take said composition and no other drugs for the following 4 weeks. At the following checkup, the subject's physician again noted that the subject was experience much more hair re-growth than typical. The subject's physician performed a scan which did not find any tumors, including metastatic tumors. Blood tests confirmed the absence of tumors. The physician advised the subject to keep taking the composition in Table 1 and monitor in the coming 6 months with no further chemotherapy during that period. By end of month 6, there were no tumors and subject felt greater energy. The subject was monitored for a further 5 years, and as no further tumors were found, the breast cancer diagnosis was cleared.

Example 5

The composition described in Table 1 was administered orally daily by a 55-year-old male subject with a diagnosis of hepatocellular carcinoma (HCC) and hepatitis C (Hep-C). The subject did not take any other medications. The subject experienced a large increase in energy after 3 weeks of daily administration. After 4 weeks of daily administration, the subject had a follow-up appointment with the original physician who diagnosed HCC and Hep-C, but standard blood tests at that appointment were unable to detect the HCC and Hep-C. CT, MRI, and liver biopsy confirmed no HCC and were unable to detect Hep-C.

Example 6

The composition described in Table 1 was orally administered daily to a 39-year-old female subject that had a history of Herpes Simplex Virus-1 (HSV-1) breakouts, averaging a breakout 2 times per week. After one week of daily oral administration, her HSV-1 breakouts stopped. Six years elapsed and the subject did not experience any more HSV-1 breakouts.

Example 7

The composition described in Table 1 was orally administered daily to a 24-year-old female subject that has had a history of Human Papillomavirus (HPV) from diagnosis by her gynecologist of genital warts. The subject experienced discomfort from the warts, but declined the HPV vaccine. On recommendation by the gynecologist, the subject began taking the composition of Table 1. At Day 10 of administration, the warts appeared to dry up and slough off. The gynecologist confirmed that the genital warts had cleared up at Day 15 of administration. Monthly checkups for the next year confirmed that the subject no longer experienced the warts and the gynecologist documented that the subject no longer had HPV.

Example 8

The composition described in Table 1 was administered daily to a 57-year-old male subject employed as an Emergency Room physician. Due to the nature of the job, the subject had a history of influenza illness every year, all year long, with clusters of more prevalent events in the Fall season. The subject documented for 5 years the dates and times of influenza events for his own case study research and had an average of 1 influenza event, lasting 1-3 days, per month. The subject began taking the composition of Table 1 during the Fall, which was usually when he experienced the most influenza events. The subject took said composition daily through December (3 months) and documented no influenza events. The subject continued to take said composition for another year and documented 0 influenza events over the next year.

Example 9

The composition described in Table 1 was orally administered daily to a 37-year-old female subject employed as an Intensive Care Unit (ICU) nurse beginning February of 2020. Despite the COVID-19 pandemic through the subsequent months and repeated contact with patients diagnosed with COVID-19, the subject did not contract COVID-19 through the end of her employment in January 2022.

Example 10

An MTT Screening Assay was designed using four cancer cell lines to aid in understanding cell viability and apoptosis. The effects of a composition described in Table 1 was tested on cancer cell viability was tested on the following 4 cell lines: A-172, glioblastoma; A-375, malignant melanoma; A-549, lung; and DU-145, prostate.

The test product was prepared for addition to cell cultures in vitro in the following manner: 0.5 g dry product was added to 5 ml of phosphate-buffered saline (PBS). The samples were allowed to sit at room temperature for an hour under gentle agitation and were then sterile-filtered through a 0.22-micron cellulose-acetate syringe filter. These filtrates were the 1:1 stock solutions, corresponding to 100 g/L product. Serial dilutions were prepared in PBS. Adding each dilution to cell cultures results in a further 10-fold dilution. This protocol was followed for preparation of product fresh on each test day, so that prepared extracts were used on the same day of preparation.

Viability testing was performed using the MTT cell viability assay. The MTT assay utilized a dye that changes color dependent on mitochondrial function, which is directly related to cellular metabolic activity and viability. Changes in metabolic activity triggered changes in MTT results while the number of viable cells is actually constant.

In the MTT bioassay, chemical reactions triggered a specific color development based on cellular functions: When a reduction in color was measured, this was linked to a reduced cellular viability, either as a result of direct killing or inhibition of mitochondrial function leading to cell death. When an increase in color was measured, this had two possible explanations: 1) Increased cell numbers (growth); 2) increased mitochondrial function (energy production). The test product was evaluated across a broad dose range (0.02 to 2 g/L).

Four different cancer cell lines were used to test serial dilutions of test products for their effects on cell viability in 48-hour cultures. Eight 2-fold serial dilutions were tested for each product, starting at 2 g/L. Testing conditions were performed in triplicate and cultures maintained at 37° C., 5% $CO_2$ for 48 hours. The viability of cells exposed to product dilutions was compared to the viability of untreated cells cultured under the same culture conditions.

In FIGS. 1A-1D, cell viability is expressed as "Percent viable cells" which is determined by comparing the optical density of cultures exposed to products to that of untreated cultures, which serve as the "100% viability" control. "*" indicates significant (p<0.05), and "**" indicates highly significant (p<0.01). Dashed line represents the viability of untreated cultures (set at 100%).

Figure 1B:
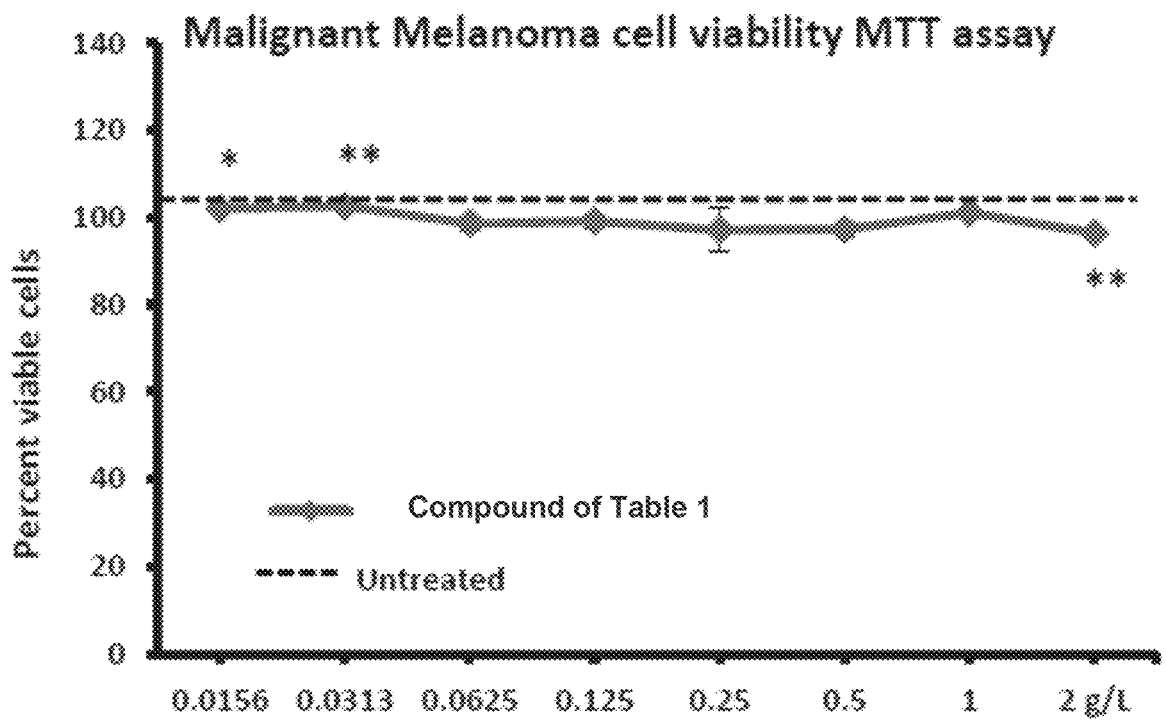
FIG. 1B is a graph showing results of an MTT screening assay of malignant melanoma cell viability.
Figure 1C:
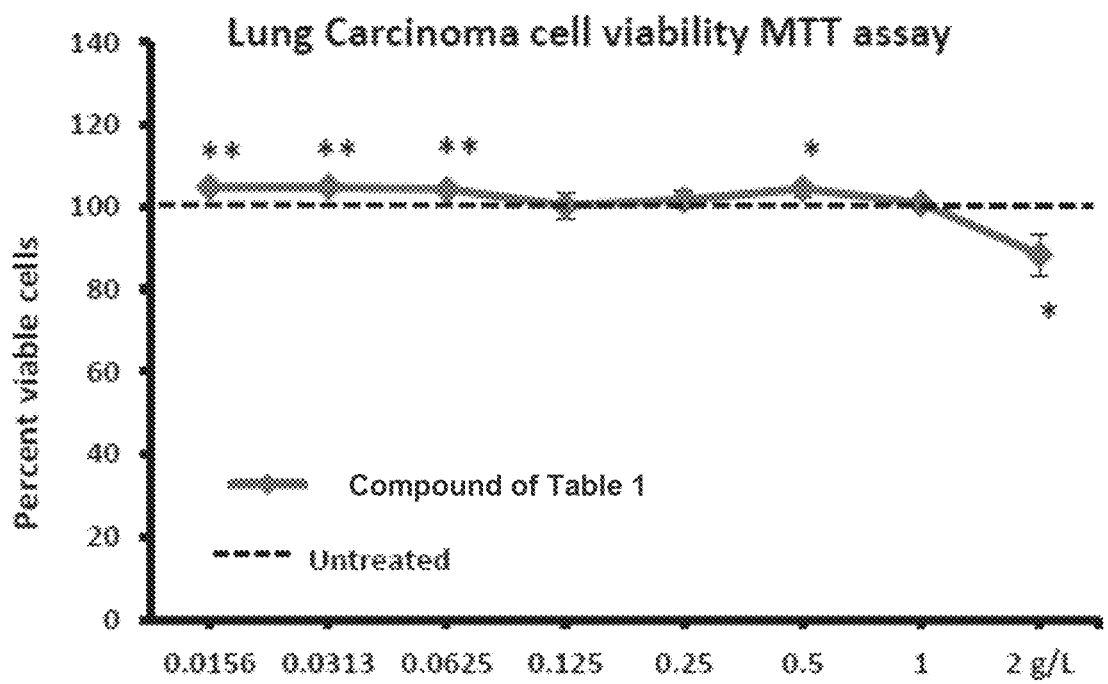
FIG. 1C is a graph showing results of an MTT screening assay of lung carcinoma cell viability.
Figure 1D:
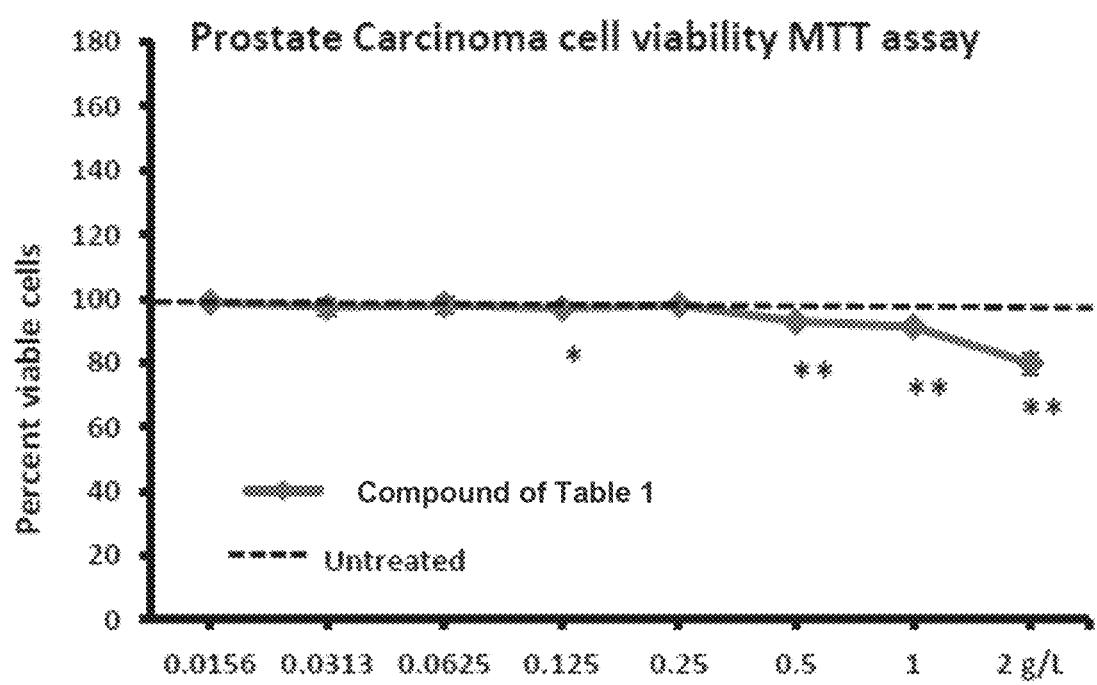
FIG. 1D is a graph showing results of an MTT screening assay of prostate carcinoma cell viability.

As shown in FIG. 1A, in the A-172, glioblastoma cell line, treatment of glioblastoma cells with the 6 highest doses led to statistically significant, dose-dependent reductions of cell viability. As shown in FIG. 1B, in the A-375, malignant melanoma cell line, treatment of malignant melanoma cells with the 4 highest doses led to a slight reduction of cell viability that was statistically significant at the 2 g/L concentration. As shown in FIG. 1C, in the A-549, lung cancer cell line, treatment of lung carcinoma cells with the highest dose led to a reduction of cell viability that was statistically significant. As shown in FIG. 1D, in the DU-145, prostate cancer cell line, treatment of prostate carcinoma cells with the 7 highest doses led to reductions of cell viability. This reduction was dose-dependent and statistically significant at the 0.125 and 0.5 to 2 g/L concentrations.

These cancer cell lines represent varied genetic profiles for cancer types and the results appear to show a broad spectrum of ability to reduce cancer cell viability using the MTT Assay.

The effects of the composition described in Table 1 on the viability of 4 different cancer cell lines was studied. Statistically significant reductions of cell viability were seen for all 4 cancer cell lines following treatment with the composition described in Table 1. Glioblastoma and prostate carcinoma cells were the most sensitive to treatment, showing a dose-dependent response. The highest dose of the composition described in Table 1 reduced the viability of malignant melanoma and lung carcinoma cells. The differences in response of all 4 cancer cell lines to the composition described in Table 1 is of strong interest. The cancer cell lines tested here represent a broad range of cancer cell types (brain, skin, lung and prostate) with differing genetic profiles, yet all 4 cancer cell lines had a statistically significant reduction in cell viability (as indicated by reduced mitochondrial function). Certain cancer cell lines (glioblastoma and prostate carcinoma) were more sensitive to treatment than others (malignant melanoma and lung carcinoma). This was not surprising since each cancer cell line possesses different genetic alterations that lead to differences in response to anti-cancer drugs and therapies. This initial pilot work is a first step in beginning to understand how consumption of the composition described in Table 1 supports health. In the special case of cancer, the data here suggest that some compounds in the composition described in Table 1 could have a direct effect on reducing the growth of cancer cells or enhancing the immune system. With the product proven safe, non-toxic, and complementary effect with traditional chemotherapy, it seems a clear option for healthy patients as a potential prevention to cancer as well as patients diagnosed with these types of cancers to help mitigate effects and/or synergize with therapy plans.

Example 11

The compound described in Table 1 was tested in an in vitro study on nine different cancer cell lines, listed below in Table A:

TABLE A

| Species | Cell Line |
|---|---|
| C3H mouse | 6C3HED lymphosarcoma |
| | SCC VII squamous cell carcinoma |
| Balb/c mouse | BM185 leukemia |
| | 4T1 mammary tumor |
| | CT26 colon |
| C57BL/6 mouse | MC38 colon carcinoma |
| | B16 melanoma |
| Human | LN18 glioblastoma |
| | MCF7 breast |

Initial results from the study showed statistically significant reductions in all nine cancer cell lines in vitro. In combination with Example 10, a total thirteen cancer cell lines of broad genetic and behavioral aspects, have been shown to be disrupted and apoptosis has been seen with the formulation described in Table 1.

Other Considerations

Headings are included herein for reference and to aid in locating various sections. These headings are not intended to limit the scope of the concepts described with respect thereto. Such concepts may have applicability throughout the entire specification.

The entirety of each patent, patent application, publication and document referenced herein hereby is incorporated by reference. Citation of any of the patents, patent applications, publications and documents is not an admission that any of the foregoing is pertinent prior art, nor does it constitute any admission as to the contents or date of these publications or documents. Their citation is not an indication of a search for relevant disclosures. All statements regarding the date(s) or contents of the documents is based on available information and is not an admission as to their accuracy or correctness.

In the foregoing description, specific details are given to provide a thorough understanding of the examples. However, it will be understood by one of ordinary skill in the art that the examples may be practiced without these specific details.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the claims.

The methods disclosed herein comprise one or more steps or actions for achieving the described method. The method steps and/or actions may be interchanged with one another without departing from the scope of the present disclosure. In other words, unless a specific order of steps or actions is required for proper operation of the method that is being described, the order and/or use of specific steps and/or actions may be modified without departing from the scope of the present disclosure.

In at least some of the described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural or singular terms herein, those having skill in the art can translate from the plural to the singular or from the singular to the plural as is appropriate to the context or application. The various singular/plural permutations may be expressly set forth herein for sake of clarity.

The embodiments illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (for example, "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (for example, about 50%, 60%, 70%, 80%, 85% or 86%) the listing includes all intermediate and fractional values thereof (for example, 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of the embodiments.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

REFERENCES

1. Newman, D. Natural Products as Sources of New Drugs over the Last 25 Years. J. Nat. Prod. 2007, 70, 461-477.
2. Jin J O, Yadav D, Madhwani K, Puranik N, Chavda V, Song M. Seaweeds in the Oncology Arena: Anti-Cancer Potential of Fucoidan as a Drug-A Review. Molecules. 2022 Sep. 16; 27 (18): 6032. doi: 10.3390/molecules27186032. PMID: 36144768; PMCID: PMC9506145.
3. Li B, Lu F, Wei X, Zhao R. Fucoidan: structure and bioactivity. Molecules. 2008 Aug. 12; 13 (8): 1671-95. doi: 10.3390/molecules13081671. PMID: 18794778; PMCID: PMC6245444.
4. Atashrazm F, Lowenthal R M, Woods G M, Holloway A F, Dickinson J L. Fucoidan and cancer: a multifunctional molecule with anti-tumor potential. Mar Drugs. 2015 Apr. 14; 13 (4): 2327-46. doi: 10.3390/md13042327. PMID: 25874926; PMCID: PMC4413214.
5. Fitton J H. Therapies from fucoidan; multifunctional marine polymers. Mar Drugs. 2011; 9 (10): 1731-1760. doi: 10.3390/md9101731. Epub 2011 Sep. 30. PMID: 22072995; PMCID: PMC3210604.
6. Vishchuk O S, Ermakova S P, Zvyagintseva T N. Sulfated polysaccharides from brown seaweeds *Saccharina japonica* and *Undaria pinnatifida*: isolation, structural characteristics, and antitumor activity. Carbohydr Res. 2011 Dec. 13; 346 (17): 2769-76. doi: 10.1016/j.carres.2011.09.034. Epub 2011 Oct. 5. PMID: 22024567.
7. Reyes M E, Riquelme I, Salvo T, Zanella L, Letelier P, Brebi P. Brown Seaweed Fucoidan in Cancer: Implications in Metastasis and Drug Resistance. Mar Drugs. 2020 Apr. 28; 18 (5): 232. doi: 10.3390/md18050232. PMID: 32354032; PMCID: PMC7281670.
8. Sanjeewa K K A, Lee J S, Kim W S, Jeon Y J. The potential of brown-algae polysaccharides for the development of anticancer agents: An update on anticancer effects reported for fucoidan and laminaran. Carbohydr Polym. 2017 Dec. 1; 177:451-459. doi: 10.1016/j.carbpol.2017.09.005. Epub 2017 Sep. 5. PMID: 28962791.
9. Ferreira S S, Passos C P, Madureira P, Vilanova M, Coimbra M A. Structure-function relationships of immunostimulatory polysaccharides: A review. Carbohydr Polym. 2015 Nov. 5; 132:378-96. doi: 10.1016/j.carbpol.2015.05.079. Epub 2015 Jun. 9. Erratum in: Carbohydr Polym. 2016 Aug. 20; 147:557-558. PMID: 26256362.
10. Millan-Linares M C, Martin M E, Rodriguez N M, Toscano R, Claro C, Bermudez B, Pedroche J, Millan F, Montserrat-de la Paz S. Nutraceutical Extract from Dulse (*Palmaria palmata* L.) Inhibits Primary Human Neutrophil Activation. Mar Drugs. 2019 Oct. 25; 17 (11): 610. doi: 10.3390/md17110610. PMID: 31731428; PMCID: PMC6891576.
11. Lopes D, Melo T, Meneses J, Abreu M H, Pereira R, Domingues P, Lillebø A I, Calado R, Domingues M R. A New Look for the Red Macroalga *Palmaria palmata*: A Seafood with Polar Lipids Rich in EPA and with Antioxidant Properties. Mar Drugs. 2019 Sep. 13; 17 (9): 533. doi: 10.3390/md17090533. PMID: 31540326; PMCID: PMC6780953.
12. Fleurance, et. Al. Seaweed in Health and Disease Prevention. 2016. Academic Press.
13. Wang, S.; Li, Y.; White, W.; Lu, J. Extracts from New Zealand *Undaria pinnatifida* Containing Fucoxanthin as Potential Functional Biomaterials against Cancer in Vitro. J. Funct. Biomater. 2014, 5, 29-42.
14. Zhao F, Guo Z, Ma Z R, Ma L L, Zhao J. Antitumor activities of *Grifola frondosa* (Maitake) polysaccharide: A meta-analysis based on preclinical evidence and quality assessment. J Ethnopharmacol. 2021 Nov. 15; 280: 114395. doi: 10.1016/j.jep.2021.114395. Epub 2021 Jul. 13. PMID: 34271115.
15. Yang Y, Gao Z, Ma Y, Teng H, Liu Z, Wei H, Lu Y, Cheng X, Hou L, Zou X. Fucoidan inhibits lymphangiogenesis by downregulating the expression of VEGFR3 and PROX1 in human lymphatic endothelial cells. Oncotarget. 2016 Jun. 21; 7 (25): 38025-38035. doi: 10.18632/oncotarget.9443. PMID: 27203545; PMCID: PMC5122369.
16. van Weelden G, Bobiński M, Okła K, van Weelden W J, Romano A, Pijnenborg J M A. Fucoidan Structure and Activity in Relation to Anti-Cancer Mechanisms. Mar Drugs. 2019; 17 (1): 32. Published 2019 Jan. 7. doi: 10.3390/md17010032
17. Hsu, H.-Y. and Hwang, P.-A. (2019), Clinical applications of fucoidan in translational medicine for adjuvant cancer therapy. Clin Trans Med, 8: e15. https://doi.org/10.1186/s40169-019-0234-9
18. Abdul Rehman Phull & Song Ja Kim (2018) *Undaria pinnatifida* a Rich Marine Reservoir of Nutritional and Pharmacological Potential: Insights into Growth Signaling and Apoptosis Mechanisms in Cancer, Nutrition and Cancer, 70:6, 956-970, DOI: 10.1080/01635581.2018.1490449
19. Lin, Y., Qi, X., Liu, H. et al. The anti-cancer effects of fucoidan: a review of both in vivo and in vitro investigations. Cancer Cell Int 20, 154 (2020). https://doi.org/10.1186/s12935-020-01233-8
20. Hsu W J, Lin M H, Kuo T C, Chou C M, Mi F L, Cheng C H, Lin C W. Fucoidan from *Laminaria japonica* exerts antitumor effects on angiogenesis and micrometastasis in triple-negative breast cancer cells. Int J Biol Macromol. 2020 Apr. 15; 149:600-608. doi: 10.1016/j.ijbiomac.2020.01.256. Epub 2020 Jan. 28. PMID: 32004612.
21. He X, Xue M, Jiang S, Li W, Yu J, Xiang S. Fucoidan Promotes Apoptosis and Inhibits EMT of Breast Cancer Cells. Biol Pharm Bull. 2019; 42 (3): 442-447. doi: 10.1248/bpb.b18-00777. PMID: 30828076.
22. Oliveira C, Granja S, Neves N M, Reis R L, Baltazar F, Silva T H, Martins A. Fucoidan from *Fucus vesiculosus* inhibits new blood vessel formation and breast tumor growth in vivo. Carbohydr Polym. 2019 Nov. 1; 223: 115034. doi: 10.1016/j.carbpol.2019.115034. Epub 2019 Jun. 28. PMID: 31426965.
23. Hsu H Y, Lin T Y, Hu C H, Shu D T F, Lu M K. Fucoidan upregulates TLR4/CHOP-mediated caspase-3 and PARP activation to enhance cisplatin-induced cytotoxicity in human lung cancer cells. Cancer Lett. 2018 Sep. 28; 432:112-120. doi: 10.1016/j.canlet.2018.05.006. Epub 2018 May 8. PMID: 29746926.
24. Chantree P, Na-Bangchang K, Martviset P. Anticancer Activity of Fucoidan via Apoptosis and Cell Cycle Arrest on Cholangiocarcinoma Cell. Asian Pac J Cancer Prev. 2021 Jan. 1; 22 (1): 209-217. doi: 10.31557/APJCP.2021.22.1.209. PMID: 33507701; PMCID: PMC8184191.
25. Xu L, Liu F, Li C, Li S, Wu H, Guo B, Gu J, Wang L. Fucoidan suppresses the gastric cancer cell malignant phenotype and production of TGF-β1 via CLEC-2. Glycobiology. 2020 Apr. 20; 30 (5): 301-311. doi: 10.1093/glycob/cwz097. PMID: 31742327.

26. Blaszczak W, Lach M S, Barczak W, Suchorska W M. Fucoidan Exerts Anticancer Effects Against Head and Neck Squamous Cell Carcinoma In Vitro. Molecules. 2018; 23 (12): 3302. Published 2018 Dec. 12. doi: 10.3390/molecules23123302
27. Chantrec P, Surarak T, Sangpairoj K, Aguilar P, Hitakomate E. Antitumor Effects of Fucoidan Via Apoptotic and Autophagic Induction on HSC-3 Oral Squamous CellCarcinoma. Asian Pac J Cancer Prev. 2020 Aug. 1; 21 (8): 2469-2477. doi: 10.31557/APJCP.2020.21.8.2469. PMID: 32856880; PMCID: PMC7771925.
28. Saitoh Y, Nagai Y, Miwa N. Fucoidan-Vitamin C complex suppresses tumor invasion through the basement membrane, with scarce injuries to normal or tumor cells, via decreases in oxidative stress and matrix metalloproteinases. Int J Oncol. 2009 November; 35 (5): 1183-9. doi: 10.3892/ijo_00000435. PMID: 19787274.
29. Thakur V, Lu J, Roscilli G, Aurisicchio L, Cappelletti M, Pavoni E, White W L, Bedogni B. The natural compound fucoidan from New Zealand *Undaria pinnatifida* synergizes with the ERBB inhibitor lapatinib enhancing melanoma growth inhibition. Oncotarget. 2017 Mar. 14; 8 (11): 17887-17896. doi: 10.18632/oncotarget.14437. PMID: 28060735; PMCID: PMC5392294.
30. Boo H J, Hong J Y, Kim S C, et al. The anticancer effect of fucoidan in PC-3 prostate cancer cells. Mar Drugs. 2013; 11 (8): 2982-2999. Published 2013 Aug. 19. doi: 10.3390/md11082982.
31. Bae H, Lee J Y, Yang C, Song G, Lim W. Fucoidan Derived from *Fucus vesiculosus* Inhibits the Development of Human Ovarian Cancer via the Disturbance of Calcium Homeostasis, Endoplasmic Reticulum Stress, and Angiogenesis. Mar Drugs. 2020 Jan. 9; 18 (1): 45. doi: 10.3390/md18010045. PMID: 31936539; PMCID: PMC7024155.
32. Pagarete, A.; Ramos, A. S.; Puntervoll, P.; Allen, M. J.; Verdelho, V. Antiviral Potential of Algal Metabolites—A Comprehensive Review. Mar. Drugs 2021, 19, 94. https://doi.org/10.3390/md19020094
33. Güven, K. C., Coban, B., & Ozdemir, O. (2020). Pharmacology of marine macroalgae. Encyclopedia of Marine Biotechnology, 1, 585-615.
34. Pradhan B, Nayak R, Patra S, Bhuyan P P, Behera P K, Mandal A K, Behera C, Ki J S, Adhikary S P, MubarakAli D, Jena M. A state-of-the-art review on fucoidan as an antiviral agent to combat viral infections. Carbohydr Polym. 2022 Sep. 1; 291:119551. doi: 10.1016/j.carbpol.2022.119551. Epub 2022 May 2. PMID: 35698330; PMCID: PMC9057937.
35. Kwon, P. S., Oh, H., Kwon, S J. et al. Sulfated polysaccharides effectively inhibit SARS-COV-2 in vitro. Cell Discov 6, 50 (2020). https://doi.org/10.1038/s41421-020-00192-8.
36. Yim, S.-K.; Kim, K.; Kim, I.-H.; Chun, S.-H.; Oh, T.-H.; Kim, J.-U.; Kim, J.-W.; Jung, W.-H.; Moon, H.-S.; Ku, B.-S.; et al. Inhibition of SARS-COV-2 Virus Entry by the Crude Polysaccharides of Seaweeds and Abalone Viscera In Vitro. Mar. Drugs 2021, 19, 219. https://doi.org/10.3390/md19040219.
37. Nidhi Hans, Anushree Malik, Satyanarayan Naik, Antiviral activity of sulfated polysaccharides from marine algae and its application in combating COVID-19: Mini review, Bioresource Technology Reports, Volume 13, 2021
38. Kiselevskiy M V, Anisimova N Y, Bilan M I, Usov A I, Ustyuzhanina N E, Petkevich A A, Shubina I Z, Morozevich G E, Nifantiev N E. Prospects for the Use of Marine Sulfated Fucose-Rich Polysaccharides in Treatment and Prevention of COVID-19 and Post-COVID-19 Syndrome. Russ J Bioorg Chem. 2022 Oct. 29:1-14. doi: 10.1134/S1068162022060152. Epub ahead of print. PMID: 36325402; PMCID: PMC9584273.
39. Oliyaei N, Moosavi-Nasab M, Mazloomi S M. Therapeutic activity of fucoidan and carrageenan as marine algal polysaccharides against viruses. 3 Biotech. 2022 July; 12 (7): 154. doi: 10.1007/s13205-022-03210-6. Epub 2022 Jun. 25. PMID: 35765662; PMCID: PMC9233728.
40. Makarenkova, I. D., et al. "Antiviral activity of sulfated polysaccharide from the brown algae *Laminaria japonica* against avian influenza A (H5N1) virus infection in the cultured cells." Voprosy virusologii 55.1 (2010): 41-45.
41. Teas J, Irhimeh M R. Dietary algae and HIV/AIDS: proof of concept clinical data. J Appl Phycol. 2012 June; 24 (3): 575-582. doi: 10.1007/s10811-011-9766-0. Epub 2011 Dec. 29. PMID: 22661829; PMCID: PMC3354323.
42. Prokofjeva M M, Imbs T I, Shevchenko N M, Spirin P V, Horn S, Fehse B, Zvyagintseva T N, Prassolov V S. Fucoidans as potential inhibitors of HIV-1. Mar Drugs. 2013 Aug. 19; 11 (8): 3000-14. doi: 10.3390/md11083000. PMID: 23966033; PMCID: PMC3766878.
43. "K. C. S. Queiroz, V. P. Medeiros, L. S. Queiroz, L. R. D. Abreu, H. A. O. Rocha, C. V. Ferreira, M. B. Jucá, H. Aoyama, E. L. Leite, Inhibition of reverse transcriptase activity of HIV by polysaccharides of brown algae, Biomedicine & Pharmacotherapy, Volume 62, Issue 5, 2008.
44. Li H, Li J, Tang Y, Lin L, Xie Z, Zhou J, Zhang L, Zhang X, Zhao X, Chen Z, Zuo D. Fucoidan from *Fucus vesiculosus* suppresses hepatitis B virus replication by enhancing extracellular signal-regulated Kinase activation. Virol J. 2017 Sep. 16; 14 (1): 178. doi: 10.1186/s12985-017-0848-8. PMID: 28915824; PMCID: PMC5603053.
45. Wozniak M, Bell T, Dénes Á, Falshaw R, Itzhaki R. Anti-HSV1 activity of brown algal polysaccharides and possible relevance to the treatment of Alzheimer's disease. Int J Biol Macromol. 2015 March; 74:530-40. doi: 10.1016/j.ijbiomac.2015.01.003. Epub 2015 Jan. 10. PMID: 25583021.
46. Harden E A, Falshaw R, Carnachan S M, Kern E R, Prichard M N. Virucidal activity of polysaccharide extracts from four algal species against herpes simplex virus. Antiviral Res. 2009 September; 83 (3): 282-9. doi: 10.1016/j.antiviral.2009.06.007. Epub 2009 Jul. 1. PMID: 19576248; PMCID: PMC2730659.
47. Thompson K D, Dragar C. Antiviral activity of *Undaria pinnatifida* against herpes simplex virus. Phytother Res. 2004 July; 18 (7): 551-5. doi: 10.1002/ptr.1487. PMID: 15305315.
48. Hemmingson, J. A., Falshaw, R., Furneaux, R. H., Thompson, K., 2006. Structure and antiviral activity of the galactofucan sulfates extracted from *Undaria pinnatifida* (Phaeophyta). J. Appl. Phycol. 18, 185. https://doi.org/10.1007/s10811-006-9096-
49. Morán-Santibañez, K.; Peña-Hernández, M. A.; Cruz-Suárez, L. E.; Ricque-Marie, D.; Skouta, R.; Vasquez, A. H.; Rodríguez-Padilla, C.; Trejo-Avila, L. M. Virucidal and synergistic activity of polyphenol-rich extracts of seaweeds against measles virus. Viruses 2018, 10, 465.
50. Zhu, C.; Cao, R.; Zhang, S. X.; Man, Y. N.; Wu, X. Z. Fucoidan inhibits the growth of hepatocellular carcinoma independent of angiogenesis. Evid. Based Complement. Altern. Med. 2013, 2013.

51. Cumashi, A.; Ushakova, N. A.; Preobrazhenskaya, M. E.; D'incecco, A.; Piccoli, A.; Totani, L.; Tinari, N.; Morozevich, G. E.; Berman, A. E.; Bilan, M. I.; et al. A comparative study of the anti-inflammatory, anticoagulant, antiangiogenic, and antiadhesive activities of nine different fucoidans from brown seaweeds. Glycobiology 2007, 17, 541-552.
52. Liang, Z.; Zheng, Y.; Wang, J.; Zhang, Q.; Ren, S.; Liu, T.; Wang, Z.; Luo, D. Low molecular weight fucoidan ameliorates streptozotocin-induced hyper-responsiveness of aortic smooth muscles in type 1 diabetes rats. J. Ethnopharmacol. 2016, 191, 341-349.
53. Zhang, Z.; Till, S.; Jiang, C.; Knappe, S.; Reutterer, S.; Scheiflinger, F.; Dockal, M. Structure-activity relationship of the pro- and anticoagulant effects of *Fucus vesiculosus* fucoidan. Thromb. Hhaemos. 2014, 111, 429-437.
54. Yang, C.; Chung, D.; Shin, I. S.; Lee, H.; Kim, J.; Lee, Y.; You, S. Effects of molecular weight and hydrolysis conditions on anticancer activity of fucoidans from sporophyll of *Undaria pinnatifida*. Int. J. Biol. Macromol. 2008, 43, 433-437.
55. Wijesekara, I.; Pangestuti, R.; Kim, S. K. Biological activities and potential health benefits of sulfated polysaccharides derived from marine algae. Carbohydr. Polym. 2011, 84, 14-21.
56. Fitton, J. H.; Stringer, D.; Karpiniec, S. S. Therapies from fucoidan: An update. Mar. Drugs 2015, 13, 5920-5946.
57. Chollet, L.; Saboural, P.; Chauvierre, C.; Villemin, J. N.; Letourneur, D.; Chaubet, F. Fucoidans in Nanomedicine. Mar. Drugs 2016, 14, 145.
58. Irhimch, M. R.; Fitton, J. H.; Lowenthal, R. M. Pilot clinical study to evaluate the anticoagulant activity of fucoidan. Blood Coagul. Fibrinolysis 2009, 20, 607-610.
59. Myers, S. P.; Mulder, A. M.; Baker, D. G.; Robinson, S. R.; Rolfe, M. I.; Brooks, L.; Fitton, J. H. Effects of fucoidan from *Fucus vesiculosus* in reducing symptoms of osteoarthritis: A randomized placebo-controlled trial. Biol. Targets Ther. 2016, 10, 81-88.
60. Shirahataet al. Fucoidan extract enhances the anti-cancer activity of chemotherapeutic agents in breast cancer cells. BMC Proceedings 2013, 7 (Suppl6): P70.
61. Kladar N V, Gavarić N S, Božin B N. *Ganoderma*: insights into anticancer effects. Eur J Cancer Prev. 2016 September; 25 (5): 462-71. doi: 10.1097/CEJ.0000000000000204. PMID: 26317382.
62. Liu, Y.; Guo, Z.-J.; Zhou, X.-W. Chinese *Cordyceps*: Bioactive Components, Antitumor Effects and Underlying Mechanism—A Review. Molecules 2022, 27, 6576. https://doi.org/10.3390/molecules27196576.
63. Patel, S., Goyal, A. Recent developments in mushrooms as anti-cancer therapeutics: a review. 3 Biotech 2, 1-15 (2012). https://doi.org/10.1007/s13205-011-0036-2.
64. Xirui He, Xiaoxiao Wang, Jiacheng Fang, Yu Chang, Ning, Hao Guo, Linhong Huang, Xiaoqiang Huang, Zefeng Zhao, Structures, biological activities, and industrial applications of the polysaccharides from *Hericium erinaceus* (Lion's Mane) mushroom: A review, International Journal of Biological Macromolecules, Volume 97, 2017, https://doi.org/10.1016/j.ijbiomac.2017.01.040.
65. Yadav S K, Ir R, Jeewon R, Doble M, Hyde K D, Kaliappan I, Jeyaraman R, Reddi R N, Krishnan J, Li M, Durairajan S S K. A Mechanistic Review on Medicinal Mushrooms-Derived Bioactive Compounds: Potential Mycotherapy Candidates for Alleviating Neurological Disorders. Planta Med. 2020 November; 86 (16): 1161-1175. doi: 10.1055/a-1177-4834. Epub 2020 Jul. 14. PMID: 32663897.
66. Chapter 11. The biological activities of the antitumor drug *Grifola frondosa* polysaccharide. Progress in Molecular Biology and Translational Science, Volume 163 #2019 Elsevier Inc. ISSN 1877-1173 All rights reserved. https://doi.org/10.1016/bs.pmbts.2019.02.010
67. Ahmad M F. *Ganoderma lucidum*: A rational pharmacological approach to surmount cancer. J Ethnopharmacol. 2020 Oct. 5; 260:113047. doi: 10.1016/j.jep.2020.113047. Epub 2020 Jun. 3. PMID: 32504783.
68. Zhang Y, Sun D, Meng Q, Guo W, Chen Q, Zhang Y. *Grifola frondosa* polysaccharides induce breast cancer cell apoptosis via the mitochondrial-dependent apoptotic pathway. Int J Mol Med. 2017 October; 40 (4): 1089-1095. doi: 10.3892/ijmm.2017.3081. Epub 2017 Jul. 26. Erratum in: Int J Mol Med. 2022 November; 50 (5): PMID: 28765878; PMCID: PMC5593468
69. Deng G, Lin H, Seidman A, Fornier M, D'Andrea G, Wesa K, Yeung S, Cunningham-Rundles S, Vickers A J, Cassileth B. A phase I/II trial of a polysaccharide extract from *Grifola frondosa* (Maitake mushroom) in breast cancer patients: immunological effects. J Cancer Res Clin Oncol. 2009 September; 135 (9): 1215-21. doi: 10.1007/s00432-009-0562-z. Epub 2009 Mar. 1. PMID: 19253021; PMCID: PMC3751581.
70. Rossi P, Difrancia R, Quagliariello V, Savino E, Tralongo P, Randazzo C L, Berretta M. B-glucans from *Grifola frondosa* and *Ganoderma lucidum* in breast cancer: an example of complementary and integrative medicine. Oncotarget. 2018 May 15; 9 (37): 24837-24856. doi: 10.18632/oncotarget.24984. PMID: 29872510; PMCID: PMC5973856.
71. Alonso, E. N., Ferronato, M. J., Fermento, M. E., Gandini, N. A., Romero, A. L., Guevara, J. A., Facchinetti, M. M., & Curino, A. C. (2018). Antitumoral and antimetastatic activity of Maitake D-Fraction in triple-negative breast cancer cells. Oncotarget, 9, 23396-23412.
72. Suárez-Arroyo I J, Rios-Fuller T J, Feliz-Mosquea Y R, et al. *Ganoderma lucidum* Combined with the EGFR Tyrosine Kinase Inhibitor, Erlotinib Synergize to Reduce Inflammatory Breast Cancer Progression. J Cancer. 2016; 7 (5): 500-511. Published 2016 Feb. 5. doi: 10.7150/jca.13599.
73. Zhang Y. *Ganoderma lucidum* (Reishi) suppresses proliferation and migration of breast cancer cells via inhibiting Wnt/β-catenin signaling. Biochem Biophys Res Commun. 2017 Jul. 8; 488 (4): 679-684. doi: 10.1016/j.bbrc.2017.04.086. Epub 2017 Apr. 17. PMID: 28427938.
74. Suárez-Arroyo I J, Loperena-Alvarez Y, Rosario-Acevedo R, Martínez-Montemayor M M. *Ganoderma* spp.: A Promising Adjuvant Treatment for Breast Cancer. Medicines (Basel). 2017 March; 4 (1): 15. doi: 10.3390/medicines4010015. Epub 2017 Mar. 15. PMID: 28758107; PMCID: PMC5533290.
75. Jiang J, Sliva D. Novel medicinal mushroom blend suppresses growth and invasiveness of human breast cancer cells. Int J Oncol. 2010 December; 37 (6): 1529-36. doi: 10.3892/ijo_00000806. PMID: 21042722.
76. Roda E, De Luca F, Di Iorio C, Ratto D, Siciliani S, Ferrari B, Cobelli F, Borsci G, Priori E C, Chinosi S, Ronchi A, Franco R, Di Francia R, Berretta M, Locatelli C A, Gregori A, Savino E, Bottone M G, Rossi P. Novel Medicinal Mushroom Blend as a Promising Supplement in Integrative Oncology: A Multi-Tiered Study using 4T1

Triple-Negative Mouse Breast Cancer Model. International Journal of Molecular Sciences. 2020; 21 (10): 3479. https://doi.org/10.3390/ijms21103479.
77. Xingguo Quan, Beom Seok Kwak, Ji-Young Lee, Jin Hee Park, Anbok Lee, Tae Hyun Kim, SaeGwang Park, "*Cordyceps militaris* Induces Immunogenic Cell Death and Enhances Antitumor Immunogenic Response in Breast Cancer", Evidence-Based Complementary and Alternative Medicine, vol. 2020, Article ID 9053274, 11 pages, 2020. https://doi.org/10.1155/2020/9053274.
78. Wei C, Khan M A, Du J, Cheng J, Tania M, Leung E L, Fu J. Cordycepin Inhibits Triple-Negative Breast Cancer Cell Migration and Invasion by Regulating EMT-TFs SLUG, TWIST1, SNAIL1, and ZEB1. Front Oncol. 2022 Jun. 14; 12:898583. doi: 10.3389/fonc.2022.898583. PMID: 35774120; PMCID: PMC9237498.
79. Zhu, J, Xu, J, Jiang, L-L, et al. Improved antitumor activity of cisplatin combined with *Ganoderma lucidum* polysaccharides in U14 cervical carcinoma-bearing mice. Kaohsiung J Med Sci. 2019; 35:222-229. https://doi.org/10.1002/kjm2.12020.
80. Panwong, S.; Wathikthinnakon, M.; Kacwkod, T.; Sawasdee, N.; Tragoolpua, Y.; Yenchitsomanus, P.-t.; Panya, A. Cordycepin Sensitizes Cholangiocarcinoma Cells to Be Killed by Natural Killer-92 (NK-92) Cells. Molecules 2021, 26, 5973. https://doi.org/10.3390/molecules26195973
81. Bie N, Han L, Wang Y, Wang X, Wang C. A polysaccharide from *Grifola frondosa* fruit body induces HT-29 cells apoptosis by PI3K/AKT-MAPKs and NF-κB-pathway. Int J Biol Macromol. 2020 Mar. 15; 147:79-88. doi: 10.1016/j.ijbiomac.2020.01.062. Epub 2020 Jan. 8. PMID: 31923503.
82. Wucheng Qi, Xingtao Zhou, Junqiao Wang, Ke Zhang, Yujia Zhou, Shuping Chen, Shaoping Nie, Mingyong Xie, *Cordyceps sinensis* polysaccharide inhibits colon cancer cells growth by inducing apoptosis and autophagy flux blockage via mTOR signaling, Carbohydrate Polymers, Volume 237, 2020
83. Zhang Z, Li K, Zheng Z, Liu Y. Cordycepin inhibits colon cancer proliferation by suppressing MYC expression. BMC Pharmacol Toxicol. 2022 Feb. 4; 23 (1): 12. doi: 10.1186/s40360-022-00551-z. PMID: 35120580; PMCID: PMC8817531.
84. Na K, Li K, Sang T, Wu K, Wang Y, Wang X. Anticarcinogenic effects of water extract of sporoderm-broken spores of *Ganoderma lucidum* on colorectal cancer in vitro and in vivo. Int J Oncol. 2017 May; 50 (5): 1541-1554. doi: 10.3892/ijo.2017.3939. Epub 2017 Mar. 29. PMID: 28358412; PMCID: PMC5403400.
85. Zhao F, Wang Y F, Song L, Jin J X, Zhang Y Q, Gan H Y, Yang K H. Synergistic Apoptotic Effect of D-Fraction From *Grifola frondosa* and Vitamin C on Hepatocellular Carcinoma SMMC-7721 Cells. Integr Cancer Ther. 2017 June; 16 (2): 205-214. doi: 10.1177/1534735416644674. Epub 2016 May 5. PMID: 27151580; PMCID: PMC5739120.
86. Mao G H, Ren Y, Feng W W, Li Q, Wu H Y, Jin D, Zhao T, Xu C Q, Yang L Q, Wu X Y. Antitumor and immunomodulatory activity of a water-soluble polysaccharide from *Grifola frondosa*. Carbohydr Polym. 2015 Dec. 10; 134:406-12. doi: 10.1016/j.carbpol.2015.08.020. Epub 2015 Aug. 12. PMID: 26428141.
87. Wu J R, Hu C T, You R I, Ma P L, Pan S M, Lee M C, Wu W S. Preclinical trials for prevention of tumor progression of hepatocellular carcinoma by LZ-8 targeting c-Met dependent and independent pathways. PLOS One. 2015 Jan. 21; 10 (1): e0114495. doi: 10.1371/journal.pone.0114495. PMID: 25607934; PMCID: PMC4301873.
88. Hu Q, Xie B. Effect of Maitake D-fraction in advanced laryngeal and pharyngeal cancers during concurrent chemoradiotherapy: A randomized clinical trial. Acta Biochim Pol. 2022 Sep. 7; 69 (3): 625-632. doi: 10.18388/abp.2020_5996. PMID: 36070433.
89. Zhong M, Huang J, Mao P, He C, Yuan D, Chen C, Zhang H, Hu J, Zhang J. *Ganoderma lucidum* polysaccharide inhibits the proliferation of leukemic cells through apoptosis. Acta Biochim Pol. 2022 Jun. 28; 69 (3): 639-645. doi: 10.18388/abp.2020_6070. PMID: 35763830.
90. Chen S N, Chang C S, Hung M H, Chen S, Wang W, Tai C J, Lu C L. The Effect of Mushroom Beta-Glucans from Solid Culture of *Ganoderma lucidum* on Inhibition of the Primary Tumor Metastasis. Evid Based Complement Alternat Med. 2014; 2014:252171. doi: 10.1155/2014/252171. Epub 2014 Apr. 1. PMID: 24799937; PMCID: PMC3995106.
91. Gill B S, Kumar S, Navgeet. Ganoderic acid targeting nuclear factor erythroid 2-related factor 2 in lung cancer. Tumour Biol. 2017 March; 39 (3): 1010428317695530. doi: 10.1177/1010428317695530. PMID: 28349780.
92. Gill B S, Navgeet, Kumar S. *Ganoderma lucidum* targeting lung cancer signaling: A review. Tumour Biol. 2017 June; 39 (6): 1010428317707437. doi: 10.1177/1010428317707437. PMID: 28653896.
93. Su C T, Wu J H. Management of Combined Therapy (Ceritinib, A. *cinnamomea*, *G. lucidum*, and Photobiomodulation) in Advanced Non-Small-Cell Lung Cancer: A Case Report. Life (Basel). 2022 Jun. 9; 12 (6): 862. doi: 10.3390/life12060862. PMID: 35743893; PMCID: PMC9228003.
94. Barbieri A, Quagliariello V, Del Vecchio V, Falco M, Luciano A, Amruthraj N J, Nasti G, Ottaiano A, Berretta M, Iaffaioli R V, Arra C. Anticancer and Anti-Inflammatory Properties of *Ganoderma lucidum* Extract Effects on Melanoma and Triple-Negative Breast Cancer Treatment. Nutrients. 2017 Feb. 28; 9 (3): 210. doi: 10.3390/nu9030210. PMID: 28264501; PMCID: PMC5372873.
95. Zhou Y, Mei X, Li Y, Yang W, Su X, Hu H. Cordycepin inhibits the proliferation and progression of NPC by targeting the MAPK/ERK and β-catenin pathways. Oncol Lett. 2022 January; 23 (1): 20. doi: 10.3892/ol.2021.13138. Epub 2021 Nov. 16. PMID: 34858524; PMCID: PMC8617562.
96. Duan L, Wu X L, Zhao F, Zeng R, Yang K H. Induction Effect to Apoptosis by Maitake Polysaccharide: Synergistic Effect of Its Combination With Vitamin C in Neuroglioma Cell. J Evid Based Complementary Altern Med. 2017 October; 22 (4): 667-674. doi: 10.1177/2156587217708524. Epub 2017 May 22. PMID: 28528571; PMCID: PMC5871285.
97. de Camargo M R, Frazon T F, Inacio K K, Smiderle F R, Amôr N G, Dionísio T J, Santos C F, Rodini C O, Lara V S. *Ganoderma lucidum* polysaccharides inhibit in vitro tumorigenesis, cancer stem cell properties and epithelial-mesenchymal transition in oral squamous cell carcinoma. J Ethnopharmacol. 2022 Mar. 25; 286:114891. doi: 10.1016/j.jep.2021.114891. Epub 2021 Dec. 12. PMID: 34910952.
98. Zhang Q H, Hu Q X, Xie D, Chang B, Miao H G, Wang Y G, Liu D Z, Li X D. *Ganoderma lucidum* Exerts an Anticancer Effect on Human Osteosarcoma Cells via Suppressing the Wnt/β-Catenin Signaling Pathway. Integr Cancer Ther. 2019 January-December; 18:1534735419890917. doi: 10.1177/1534735419890917. PMID: 31855073; PMCID: PMC6923688.

99. Jang H J, Yang K E, Hwang I H, Huh Y H, Kim D J, Yoo H S, Park S J, Jang I S. Cordycepin inhibits human ovarian cancer by inducing autophagy and apoptosis through Dickkopf-related protein 1/β-catenin signaling. Am J Transl Res. 2019 Nov. 15; 11 (11): 6890-6906. PMID: 31814895; PMCID: PMC6895532.

100. Li X Y, Tao H, Jin C, D U Z Y, Liao W F, Tang Q J, Ding K. Cordycepin inhibits pancreatic cancer cell growth in vitro and in vivo via targeting FGFR2 and blocking ERK signaling. Chin J Nat Med. 2020 May; 18 (5): 345-355. doi: 10.1016/S1875-5364 (20) 30041-8. PMID: 32451092.

101. Zhang Y, Zhang G, Ling J. Medicinal Fungi with Antiviral Effect. Molecules. 2022 Jul. 12; 27 (14): 4457. doi: 10.3390/molecules27144457. PMID: 35889330; PMCID: PMC9322162.

102. Hetland G, Johnson E, Bernardshaw S V, Grinde B. Can medicinal mushrooms have prophylactic or therapeutic effect against COVID-19 and its pneumonic superinfection and complicating inflammation? Scand J Immunol. 2021 January; 93 (1): e12937. doi: 10.1111/sji.12937. Epub 2020 Jul. 29. PMID: 32657436; PMCID: PMC7404338.

103. Rahman M A, Rahman M S, Bashir N M B, Mia R, Hossain A, Saha S K, Kakon A J, Sarker N C. Rationalization of Mushroom-Based Preventive and Therapeutic Approaches to COVID-19: Review. Int J Med Mushrooms. 2021; 23 (5): 1-11. doi: 10.1615/IntJMedMushrooms.2021038285. PMID: 34347990.

104. Akalesh Kumar Verma (2022) Cordycepin: a bioactive metabolite of Cordyceps militaris and polyadenylation inhibitor with therapeutic potential against COVID-19, Journal of Biomolecular Structure and Dynamics, 40:8, 3745-3752, DOI: 10.1080/07391102.2020.1850352.

105. Stamets, Paul & Naeger, Nicholas & Evans, Jay & Han, Jennifer & Hopkins, Brandon & Lopez, Dawn & Moershel, Henry & Nally, Regan & Sumerlin, David & Taylor, Alex & Carris, Lori & Sheppard, Walter. (2018). Extracts of Polypore Mushroom Mycelia Reduce Viruses in Honey Bees. Scientific Reports. 8. 10.1038/s41598-018-32194-8.

106. Zhao C, Gao L, Wang C, Liu B, Jin Y, Xing Z. Structural characterization and antiviral activity of a novel heteropolysaccharide isolated from Grifola frondosa against enterovirus 71. Carbohydr Polym. 2016 Jun. 25; 144:382-9. doi: 10.1016/j.carbpol.2015.12.005. Epub 2015 Dec. 30. PMID: 27083830.

107. Krupodorova, T., Rybalko, S. & Barshteyn, V. Antiviral activity of Basidiomycete mycelia against infuenza type A (serotype H1N1) and herpes simplex virus type 2 in cell culture. Virol. Sin. 29, 284-290 (2014).

108. El-Mekkawy, S. et al. Anti-HIV-1 and anti-HIV-1-protease substances from Ganoderma lucidum. Phytochemistry 49, 1651-1657 (1998).

109. Gao Y, Zhou S, Chen G, Dai X, Ye J A (2002) Phase I/II study of a Ganoderma lucidum extract (Ganopoly) in patients with advanced cancer. IntJ Med Mushrooms 4:207-214.

110. Gao Y, Zhou Sh, Huang M, Xu A (2003) Antibacterial and antiviral value of the genus Ganoderma P. Karst. species (Aphyllophoromycetideae): a review. Int J Med Mushrooms 5:235-246.

111. Gao Y, LanJ, Dai X, Ye J, Zhou Sh (2004) A phase I/II study of Ling Zhi mushroom Ganoderma lucidum (W.Curt.: Fr.) Lloyd (Aphyllophoromycetideae) extract in patients with type II diabetes mellitus. Int J Med Mushrooms 6:96-107.

112. Didukh M Y, Wasser S P, Nevo E (2003) Medicinal value of species of the family Agaricaceae Cohn (higher Basidiomycetes) current stage of knowledge and future perspectives. Int J Med Mushrooms 5:133-152.

113. Rowan N J, Smith J E, Sullivan R (2003) Immunomodulatory activities of mushroom glucans and polysaccharide-protein complexes in animals and humans (a review). Int J Med Mushrooms 5:95-110.

114. Sullivan R, Smith J E, Rowan N J (2006) Medicinal mushrooms and cancer therapy. Translating a traditional practice into Western medicine. Perspect Biol Med 49:159-170.

115. Zhang M, Cui S W, Cheung P C K, Wang Q (2007) Antitumor polysaccharides from mushrooms: a review on their isolation, structural characteristics and antitumor activity. Trends Food Sci Technol 18:4-19.

116. Dotan N, Wasser S P, Mahajna J (2010) The culinary-medicinal mushroom Coprinus comatus as a natural anti-androgenic modulator. Integr Cancer Ther XX: 1-12.

117. Wasser S P (2010) Medicinal mushroom science: history, current status, future trends, and unsolved problems. Int J Med Mushrooms 12 (1): 1-16

118. Ivette, S. et. al. Ganoderma lucidum Combined with the EGFR Tyrosine Kinase Inhibitor, Erlotinib Synergize to Reduce Inflammatory Breast Cancer Progression. Journal of Cancer. 2016; 7 (5): 500-511.

119. Yanshree; Yu, W. S.; Fung, M. L.; Lee, C. W.; Lim, L. W.; Wong, K. H. The Monkey Head Mushroom and Memory Enhancement in Alzheimer's Disease. Cells 2022, 11, 2284. https://doi.org/10.3390/cells11152284

120. Saitsu Y, Nishide A, Kikushima K, Shimizu K, Ohnuki K. Improvement of cognitive functions by oral intake of Hericium erinaceus. Biomed Res. 2019; 40 (4): 125-131. doi: 10.2220/biomedres.40.125. PMID: 31413233.

121. Tripodi, F.; Falletta, E.; Leri, M.; Angeloni, C.; Beghelli, D.; Giusti, L.; Milanesi, R.; Sampaio-Marques, B.; Ludovico, P.; Goppa, L.; et al. Anti-Aging and Neuroprotective Properties of Grifola frondosa and Hericium erinaceus Extracts. Nutrients 2022, 14, 4368. https://doi.org/10.3390/nu14204368

122. Alessandra-Perini J, Rodrigues-Baptista K C, Machado D E, Nasciutti L E, Perini J A (2018) Anticancer potential, molecular mechanisms and toxicity of Euterpe oleracea extract (açaí): A systematic review. PLOS ONE 13 (7): e0200101. https://doi.org/10.1371/journal.pone.0200101.

123. "Silva, M. A. C. N. d.; Costa, J. H.; Pacheco-Fill, T.; Ruiz, A. L. T. G.; Vidal, F. C. B.; Borges, K. R. A.; Guimarães, S. J. A.; Azevedo-Santos, A. P. S. d.; Buglio, K. E.; Foglio, M. A.; et al. Açai (Euterpe oleracea Mart.) Seed Extract Induces ROS Production and Cell Death in MCF-7 Breast Cancer Cell Line. Molecules 2021, 26, 3546. https://doi.org/10.3390/molecules26123546

124. Marcos Antonio Custódio Neto da Silva, Camila Simões Soares, Kátia Regina Assunção Borges, Laís Araujo Souza Wolff, Maria Do Carmo Lacerda Barbosa, Maria Do Desterro Soares Brandão Nascimento & João Ernesto de Carvalho (2022) Ultrastructural changes induced by açaí (Euterpe oleracea Mart) in MCF-7 breast cancer cell line, Ultrastructural Pathology, DOI: 10.1080/01913123.2022.2141404

125. Fuentes, M. V.; Muehlmann, L. A.; Longo, J. P. F.; Silva, J. R.; Fascineli, M. L.; Souza, P.; Azevedo, R. B.

Photodynamic therapy mediated by acai oil (*Euterpe oleracea* Martius) in nanoemulsion: A potential treatment for melanoma. J. Photochem. Photobiol. B Biol. 2017, 166, 301-310.
126. Jobim, M. L.; Barbisan, F.; Fortuna, M.; Teixeira, C. F.; Boligon, A. A.; Ribeiro, E. E.; Cruz, I. B. M. Açai (*Euterpe oleracea*, Mart.), an Amazonian fruit has antitumor effects on prostate cancer cells. Arch. Biosci. Health 2019, 1, 61-76.
127. Santos O V D, Pinaffi Langley ACDC, Mota de Lima A J, Vale Moraes V S, Dias Soares S, Teixeira-Costa B E. Nutraceutical potential of Amazonian oilseeds in modulating the immune system against COVID-19-A narrative review. J Funct Foods. 2022 July; 94:105123. doi: 10.1016/j.jff.2022.105123. Epub 2022 May 24. PMID: 35634457; PMCID: PMC9127052.
128. Chia T, Nakamura T, Amano M, Takamune N, Matsuoka M, Nakata H. 2021. A small molecule, ACAi-028, with anti-HIV-1 activity targets a novel hydrophobic pocket on HIV-1 capsid. Antimicrob Agents Chemother 65: e01039-21. https://doi.org/10.1128/AAC.01039-21.
129. Yasukazu Saitoh, *Yuko* Nagai, Nobuhiko Miwa. Fucoidan-Vitamin C complex suppresses tumor invasion through the basement membrane, with scarce injuries to normal or tumor cells, via decreases in oxidative stress and matrix metalloproteinases. International Journal of Oncology. November 2009 Vol35 No 5.
130. Schauss, A G. Et. al. Antioxidant capacity and other bioactivities of the freeze-dried Amazonian palm berry, *Euterpe* oleraceae mart. (acai). J. AgricFood Chem. 2006 Nov. 1; 54 (22): 8604-10.
131. Remigante, A.; Spinelli, S.; Straface, E.; Gambardella, L.; Caruso, D.; Falliti, G.; Dossena, S.; Marino, A.; Morabito, R. Açaì (*Euterpe oleracea*) Extract Protects Human Erythrocytes from Age-Related Oxidative Stress. Cells 2022, 11, 2391. https://doi.org/10.3390/cells11152391
132. Al Monla, R.; Dassouki, Z.; Sari-Chmayssem, N.; Mawlawi, H.; Gali-Muhtasib, H. Fucoidan and Alginate from the Brown Algae Colpomenia sinuosa and Their Combination with Vitamin C Trigger Apoptosis in Colon Cancer. Molecules 2022, 27, 358.
133. Konno S. Synergistic potentiation of D-fraction with vitamin C as possible alternative approach for cancer therapy. Int J Gen Med. 2009; 30:91-108.
134. Fei Zhao, et. al. "Synergistic Apoptotic Effect of D-Fraction From *Grifola frondosa* and Vitamin C on Hepatocellular Carcinoma SMMC-7721 Cells." Integrative Cancer Therapies 2017, Vol. 16 (2) 205-214
135. Fei Zhao, et. al. "The induction of apoptosis and autophagy in human hepatoma SMMC-7721 cells by combined treatment with vitamin C and polysaccharides extracted from *Grifola frondosa*." Apoptosis. 11 Sep. 2017

What is claimed is:

1. A method of inhibiting cancer growth in an individual, the method comprising:
    administering to the individual a composition comprising:
        about 150 to about 450 mg of *Laminaria japonica*,
        about 200 to about 400 mg of *Undaria pinnatifida*,
        about 200 to about 400 mg of *Grifola frondosa*,
        about 200 to about 400 mg of *Ganoderma lucidum*,
        about 200 to about 400 mg of *Hericium erinaceus*,
        about 200 to about 400 mg of *Palmaria palmata*,
        about 200 to about 350 mg of *Fucus vesiculosus*,
        about 200 to about 350 mg of *Cordyceps sinensis*, and
        about 150 to about 350 mg of *Euterpe oleracea*,
    wherein the cancer is ovarian cancer.
2. The method of claim 1, further comprising identifying an individual having a cancer or at risk of having a cancer.
3. The method of claim 2, wherein administering comprises daily administration.
4. The method of claim 1, wherein the composition comprises about 250 mg of *Palmaria palmata*.
5. The method of claim 4, wherein the composition comprises about 250 mg of *Hericium erinaceus*.
6. The method of claim 5, wherein the composition comprises:
    about 300 mg of *Laminaria japonica*,
    about 250 mg of *Undaria pinnatifida*,
    about 250 mg of *Palmaria palmata*,
    about 250 mg of *Fucus vesiculosus*,
    about 250 mg of *Grifola frondosa*,
    about 300 mg of *Ganoderma lucidum*,
    about 250 mg of *Hericium erinaceus*,
    about 250 mg of *Cordyceps sinensis*, and
    about 200 mg of *Euterpe oleracea*.
7. The method of claim 6, wherein the composition is provided in the form of capsules or tablets.
8. The method of claim 7, wherein administering comprises oral administration.
9. The method of claim 1, wherein the composition comprises about 250 mg of *Cordyceps sinensis*, and about 200 mg of *Euterpe oleracea*.
10. The method of claim 1, wherein the composition further comprises vitamin A, vitamin C, vitamin D, Vitamin E, Thiamin, Riboflavin, Niacin, Vitamin B6, Folic Acid, Vitamin B12, Pantothenic Acid, Calcium, or a combination thereof.
11. The method of claim 10, wherein the composition comprises between 3,000-7,000 IU of vitamin A, between 30-90 mg of vitamin C, between 300-700 IU of vitamin D, between 20-80 IU of vitamin E, between 1.0-2.0 mg thiamin, between 0.8-2.5 mg of riboflavin, between 10-50 mg niacin, between 0.8-4 mg vitamin B6, between 200-800 mcg of folic acid, between 2-10 mcg of vitamin B12, between 5-20 mg pantothenic acid, and between 20-70 mg of calcium.
12. The method of claim 11, wherein the composition comprises 5000 IU vitamin A, 60 mg of vitamin C, 400 IU of vitamin D, 30 IU of vitamin E, 1.5 mg thiamin, 1.7 mg of riboflavin, 20 mg niacin, 2 mg vitamin B6, 400 mcg of folic acid, 6 mcg of vitamin B12, 10 mg pantothenic acid, and 45 mg of calcium.
13. The method of claim 6, wherein the composition further comprises vitamin A, vitamin C, vitamin D, Vitamin E, Thiamin, Riboflavin, Niacin, Vitamin B6, Folic Acid, Vitamin B12, Pantothenic Acid, Calcium, or a combination thereof.
14. The method of claim 13, wherein the composition comprises between 3,000-7,000 IU of vitamin A, between 30-90 mg of vitamin C, between 300-700 IU of vitamin D, between 20-80 IU of vitamin E, between 1.0-2.0 mg thiamin, between 0.8-2.5 mg of riboflavin, between 10-50 mg niacin, between 0.8-4 mg vitamin B6, between 200-800 mcg of folic acid, between 2-10 mcg of vitamin B12, between 5-20 mg pantothenic acid, and between 20-70 mg of calcium.
15. The method of claim 14, wherein the composition comprises 5000 IU vitamin A, 60 mg of vitamin C, 400 IU of vitamin D, 30 IU of vitamin E, 1.5 mg thiamin, 1.7 mg of riboflavin, 20 mg niacin, 2 mg vitamin B6, 400 mcg of folic acid, 6 mcg of vitamin B12, 10 mg pantothenic acid, and 45 mg of calcium.

16. The method of claim of claim 1, wherein the ovarian cancer in an ovarian tumor.

17. The method of claim of claim 1, wherein the composition is provided in the form of a powder or granule.

18. The method of claim of claim 6, wherein the composition is provided in the form of a powder or granule.

19. The method of claim of claim 1, wherein the composition is provided in the form of a liquid.

20. The method of claim of claim 6, wherein the composition is provided in the form of a liquid.

* * * * *